US006420475B1

(12) United States Patent
Chen

(10) Patent No.: US 6,420,475 B1
(45) Date of Patent: Jul. 16, 2002

(54) TEAR RESISTANT ELASTIC CRYSTAL GELS GEL COMPOSITES AND THEIR USES

(75) Inventor: John Y. Chen, Pacifica, CA (US)

(73) Assignee: Applied Elastomerics, Inc., South San Francisco, CA (US)

( * ) Notice: Subject to any disclaimer, the term of this patent is extended or adjusted under 35 U.S.C. 154(b) by 0 days.

(21) Appl. No.: 09/274,498

(22) Filed: Mar. 28, 1999

Related U.S. Application Data

(63) Continuation-in-part of application No. 09/130,545, filed on Aug. 8, 1998, and a continuation-in-part of application No. 08/984,459, filed on Dec. 3, 1997, and a continuation-in-part of application No. PCT/US97/17534, filed on Sep. 30, 1997, and a continuation-in-part of application No. 08/909,487, filed on Jul. 12, 1997, and a continuation-in-part of application No. 08/863,794, filed on May 27, 1997, and a continuation-in-part of application No. 08/819,675, filed on Mar. 17, 1997, now Pat. No. 5,884,639, and a continuation-in-part of application No. 08/719,817, filed on Sep. 30, 1996, and a continuation-in-part of application No. 08/665,343, filed on Jun. 17, 1996, which is a continuation-in-part of application No. 08/612,586, filed on Mar. 8, 1996, application No. 09/274,498, which is a continuation-in-part of application No. 08/581,125, filed on Dec. 29, 1995, now Pat. No. 5,962,572, and a continuation-in-part of application No. 08/581,191, filed on Dec. 29, 1995, now Pat. No. 5,760,117, and a continuation-in-part of application No. 08/581,188, filed on Dec. 29, 1995, now abandoned, said application No. 08/581,125, is a continuation-in-part of application No. 08/288,690, filed on Aug. 11, 1994, now Pat. No. 5,633,286, and a continuation-in-part of application No. PCT/US94/07314, filed on Jun. 27, 1994, which is a continuation-in-part of application No. PCT/US94/04278, filed on Apr. 19, 1994, said application No. 08/581,191, is a continuation-in-part of application No. 08/288,690, and a continuation-in-part of application No. PCT/US94/07314, said application No. 08/581,188, is a continuation-in-part of application No. 08/288,690, and a continuation-in-part of application No. PCT/US94/07314.

(51) Int. Cl.[7] .................. C08L 53/00; C08L 73/00; C08L 75/00; A61F 2/00
(52) U.S. Cl. ............ 524/505; 524/487; 524/507; 524/508; 524/578; 524/513; 524/515; 523/105; 523/113
(58) Field of Search ............... 523/113, 105; 524/487, 505, 507, 508, 578

(56) References Cited

U.S. PATENT DOCUMENTS 3,660,849 A   5/1972   Jonnes ............... 2/2.1
3,821,148 A   6/1974   Makowski (List continued on next page.)

FOREIGN PATENT DOCUMENTS

| GB | 1268431 | 1/1969 |
| WO | PCT/WO 88/00603 | 1/1988 |
| WO | PCT/WO 90/05166 | 5/1990 |
| WO | PCT/WO 91/05014 | 4/1991 |
| WO | PCT/WO 93/05113 | 3/1993 |
| WO | PCT/WO 93/23472 | 11/1993 |

OTHER PUBLICATIONS

"SiloLiner" Sales literature from Knit–Rite medical (Mar. 1, 1999 three pages).
ALPS South Corporation –Gel Liners: NEW! Easy Liner ELPX, ELDT and ELFR published fact sheet downloaded from the Internet on Aug. 10, 1999.
Chung P. Park and George P. Clingerman, "Compatibilization of Polyethylene–Polystyrene Blends with Ethylene–Styrene Random Copolymers", the Dow Chemical Company, May 1996.
Steve Hoenig, Bob Turley and Bill Van Volkenburgh, "Material Properties and Applications of Ethylene–Styrene Interpolymers", the Dow Chemical Company, Sep. 1996.
Y. Wilson Cheung and Martin J. Guest, "Structure, Thermal Transitions and Mechanical Properties of Ethylene/Styrene Copolymers", the Dow Chemical Company, May 1996, (17).
Teresa Plumley Karjaia, Y. Wilson Cheung and Martin J. Guest, "Melt Rheology and Processability of Ethylene/ Styrene Interpolymers", the Dow Chemical Company, May 1997.
D. C. Prevorsek, et al., Origins of Damage Tolerance in Ultrastrong Polyethylene Fibers and Composites:, Journal of Polymer Science: Polymer Symposia No. 75,81–104 (1993).
Chen, H., et al, "Classification of Ethylene–Styrene Interpolymers Based on Comonomer Content", J. Appl. Polym. Sci., 1998, 70, 109.
Alizadeh, et al., "Effect of Topological Constraints on The Crystallization Behavior of Ethylene/alpha–Olefin Copolymers", PMSE, vol, 81, pp. 248–249, Aug. 22–26, 1999.
Guest, et al., "Structre/Property Relationships of Semi–Crystalline Ethylene–Styrene Interpolymers (ESI)", PMSE, vol. 81, pp. 371–372, Aug. 22–26, 1999.
"Styrene–Diene Triblock Copolymers: Orientation Conditions and Mechanical Properties of the Oriented Materials" A. Weill and R. Pixa, Journal of Polymer Science Polymer Symposium 58, 381–394 (1977).
Tuftec Trade Literature, Asani Chemical Co., Ltd., Synthetic Rubber Division, English and Japanese 14 Pages.
Septon Trade Literature, Kuraray Co., Ltd. 1995.8 (4,000) 15 Pages.
Shell Chemical Co., Data Sheets: EKP–207 (093094–02) and L–1203 (SC:2384–950.
SC: 1102–89 Shell Chemical Technical Bulletin *Kraton® Thermoplastic Rubber in Oil Gels*, Apr. 1989.

(List continued on next page.)

*Primary Examiner*—Kriellion Sanders

(57) ABSTRACT

Novel crystal gels and articles are formed from one or more copolymers having at least one crystalline poly(ethylene) components and high levels of a plasticizer, said midblock segment having an amount of crystallinity sufficient to achieve improvements in one or more physical properties including improved crack propagation resistance, improved tear resistance, improved resistance to fatigue and resistance to catastrophic failure not obtainable in amorphous gels.

14 Claims, 5 Drawing Sheets

U.S. PATENT DOCUMENTS

| | | | |
|---|---|---|---|
| 3,821,149 A | 6/1974 | Makowski | 260/30.6 R |
| 3,827,999 A | 8/1974 | Crossland | 260/33.6 |
| 3,860,013 A | 1/1975 | Czapor | 132/91 |
| 4,136,699 A | 1/1979 | Collins | 128/290 |
| 4,151,057 A | 4/1979 | St. Clair | |
| 4,176,240 A | 11/1979 | Sabia | 174/23 |
| 4,259,540 A | 3/1981 | Sabia | |
| 4,351,913 A | 9/1982 | Patel | |
| 4,361,508 A | 11/1982 | Bourland | 523/173 |
| 4,369,284 A | 1/1983 | Chen | |
| 4,432,607 A | 2/1984 | Levy | 350/96.34 |
| 4,492,428 A | 1/1985 | Levy | |
| 4,497,538 A | 2/1985 | Patel | |
| 4,509,821 A | 4/1985 | Stenger | 350/96.23 |
| 4,600,261 A | 7/1986 | Debbaut | |
| 4,610,738 A | 9/1986 | Jervis | 156/49 |
| 4,618,213 A | 10/1986 | Chen | |
| 4,643,924 A | 2/1987 | Uken | 428/35 |
| 4,662,692 A | 5/1987 | Uken | 339/96 |
| 4,678,664 A | 7/1987 | Schmolka | 424/65 |
| 4,680,233 A | 7/1987 | Camin | 428/424.6 |
| 4,690,831 A | 9/1987 | Uken | 427/44 |
| 4,692,369 A | 9/1987 | Nomi | 428/198 |
| 4,709,982 A | 12/1987 | Corne | 427/44 |
| 4,716,183 A | 12/1987 | Gamarra | 522/90 |
| 4,721,832 A | 1/1988 | Toy | 174/87 |
| 4,764,535 A | 8/1988 | Leicht | |
| 4,798,853 A | 1/1989 | Handlin | 523/173 |
| 4,801,346 A | 1/1989 | Huddleston | |
| 4,822,834 A | 4/1989 | Blevins | 524/427 |
| 4,833,193 A | 5/1989 | Sieverding | |
| 4,842,931 A | 6/1989 | Zook | 428/354 |
| 4,864,725 A | 9/1989 | Debbaut | 29/871 |
| 4,865,905 A | 9/1989 | Uken | 428/220 |
| 4,880,676 A | 11/1989 | Pulgcerver | 428/35.7 |
| 4,880,878 A | 11/1989 | Himes | 525/89 |
| 4,883,431 A | 11/1989 | Uken | |
| 4,888,070 A | 12/1989 | Clark | |
| 4,889,171 A | 12/1989 | Covington | 428/304 |
| 4,889,403 A | 12/1989 | Zucker | |
| 4,900,877 A | 2/1990 | Dubrow | 174/35 |
| 4,909,756 A | 3/1990 | Jervis | |
| 4,929,211 A | 5/1990 | Resnick | 446/14 |
| 4,942,270 A | 7/1990 | Gamarra | 174/93 |
| 4,944,363 A | 7/1990 | Osher | 273/58 |
| 4,944,973 A | 7/1990 | Follette | |
| 4,968,747 A | 11/1990 | Mallikarjun | 525/74 |
| 4,983,008 A | 1/1991 | Campbell | 350/96.16 |
| 5,026,054 A | 6/1991 | Osher | 273/58 |
| 5,059,748 A | 10/1991 | Allen | 174/87 |
| 5,068,138 A | 11/1991 | Mitchell | 428/36.8 |
| 5,085,597 A | 2/1992 | Story | 439/521 |
| 5,088,734 A | 2/1992 | Glava | 273/73 |
| 5,098,421 A | 3/1992 | Zook | 604/367 |
| 5,126,182 A | 6/1992 | Douglas | 428/90 |
| 5,149,736 A | 9/1992 | Gamarra | 524/490 |
| 5,153,254 A | 10/1992 | Chen | 524/505 |
| 5,159,022 A | 10/1992 | Ikematu | 525/250 |
| 5,167,649 A | 12/1992 | Zook | 604/307 |
| 5,173,573 A | 12/1992 | Jervis | 174/138 |
| 5,177,143 A | 1/1993 | Toy | 524/848 |
| 5,181,914 A | 1/1993 | Zook | 604/307 |
| 5,191,752 A | 3/1993 | Murphy | 54/44.5 |
| 5,221,534 A | 6/1993 | Deslauriers | 424/78.03 |
| 5,239,723 A | 8/1993 | Chen | 15/104 |
| 5,262,468 A | * 11/1993 | Chen | 524/476 |
| 5,313,019 A | 5/1994 | Brusselmans | 174/93 |
| 5,324,222 A | 6/1994 | Chen | 446/34 |
| 5,330,452 A | 7/1994 | Zook | 604/307 |
| 5,334,646 A | 8/1994 | Chen | 524/474 |
| 5,336,708 A | * 8/1994 | Chen | 524/474 |
| 5,459,193 A | 10/1995 | Anderson | 524/505 |
| 5,475,890 A | 12/1995 | Chen | 15/104 |
| 5,479,952 A | 1/1996 | Zachariades | 132/321 |
| 5,559,165 A | 9/1996 | Paul | 523/111 |
| 5,606,149 A | 2/1997 | Yaworski | 174/92 |
| 5,618,882 A | 4/1997 | Hammond | 525/92 D |
| 5,624,294 A | 4/1997 | Chen | 446/253 |
| 5,626,657 A | 5/1997 | Pearce | 106/122 |
| 5,633,286 A | 5/1997 | Chen | 524/474 |
| 5,655,947 A | 8/1997 | Chen | 446/46 |
| 5,863,977 A | 1/1999 | Fisher | |
| 5,872,201 A | 2/1999 | Cheung | |
| 5,929,138 A | 7/1999 | Mercer | |
| 5,952,396 A | 9/1999 | Chang | 522/1 |
| 5,994,446 A | 11/1999 | Graykys | |
| 5,994,450 A | 11/1999 | Pearce | 524/505 |

OTHER PUBLICATIONS

"TUFTEC"—its characteristics and applications, Assahi Chemical.

Septon, High Performance Thermoplastic Rubber, Kurraray Co., Ltd., 1995.

Kraton Polymers, May 1997, Shell Chemical Company.

Silipos product catlouge.

Silipos products catlouge sheets: Silosheath, Pressure Ulcers, Friction Sleeves with Gel, Gel–E–Rol & Friction Tape, Mesh Tubing, Silopad.

Silipos manual, 1994.

Melt Miscibility In Blends of Polypropylene, Polystryenhe––Block–Poly (Ethylene–Sat–Butylene)–Block–Polystyrene, and Processing Oil From Melting Point Depression, Ohlesson et al., Polymer Engineering and Science, 1996, vol. 36, No. 11.

Blends And Thermoplastic Interpenetrating Polymer Networks Of Polypropytlene And Polystyrene–Block–Poly (Ethylene–Stat–Butylene)–Block–Polytstyrene Triblock Copolymer. 1: Morphology And Structure–Related Properties, Ohlesson, et al., Polymer Engineering and Science, Feb. 1996, vol. 36, No. 4.

Migration And Blooming Of Waxes To The Surface Of Rubber Vulcanizates, Nah, et al., J. Of Polymer Science: Polymer Physics Ed., vol. 18, 511–521 (1980).

* cited by examiner

| | |
|---|---|
| M1 | Fabric or Cloth |
| G | Gel |
| GM | Gel-Sponge or Gel-Foam |
| M2 | Foam or Sponge |
| M3 | Synthetic Resin or Plastic |
| M4 | Fibre |
| M5 | Concrete |
| M6 | Metal or Metal Sponge |
| M7 | Wood |
| M8 | Wire or Screening |
| M9 | Refractory Material |
| M10 | Other Material |

Figure 1

TEAR RESISTANT ELASTIC CRYSTAL GELS GEL COMPOSITES AND THEIR USES

RELATED APPLICATIONS

This application is a continuation-in-part of the following applications: U.S. Ser. Nos: Ser. No. 09/130,545 filed Aug. 8, 1998; Ser. No. 08/984,459, filed Dec. 3, 1997; Ser. No. 08/909,487, filed Jul. 12, 1997; Ser. No. 08/863,794, filed May 27, 1997; Ser. No. 08/819,675, filed Mar. 17, 1997 now U.S. Pat. No. 5,884,639; PCT/US97/17534, filed Sep. 30, 1997 now Ser. No. 09/230,940 filed Feb. 3, 1999; Ser. No. 08/719,817, filed Sep. 30, 1996; Ser. No; 08/665,343, filed Jun. 17, 1996 which is a CIP Ser. No. 08/612,586, filed Mar. 8, 1996; PCT/US94/04278, filed Apr. 19, 1994 now Ser. No. 08/211,781 filed May 14, 1996, U.S. Pat. No. 6,033,283; PCT/US94/07314, filed Jun. 27, 1994 now Ser. No. 08/256,235 filed Jun. 27, 1994 and U.S. Pat. No. 5,868,597; Ser. No. 08/288,690, filed Aug. 11, 1994 now U.S. Pat. No. 5,633,286; Ser. No. 08/581,188, filed Dec. 29, 1995 now abandoned; Ser. No. 08/581,191, filed Dec. 29, 1995 now U.S. Pat. No. 5,760,117; and Ser. No. 08/581,125, filed Dec. 29, 1995 now U.S. Pat. No. 5,962,572. In turn Ser. Nos. 08/581,188; 08/581,191; and 08/581,125 are CIP of the following applications: Ser. Nos.: Ser. No. 08/288,690 filed Aug. 11, 1994 now U.S. Pat. No. 5,633,286 and PCT/US94/07314 filed Jun. 27, 1994 which in turn is a CIP of PCT/US94/04278, filed Apr. 19, 1994. The above patents and applications are specifically incorporated herein by reference.

FIELD OF THE INVENTION

The present invention is directed to novel gels and their uses.

BACKGROUND OF THE INVENTION

Like (SEPS) poly(styrene-ethylene-propylene-styrene), random mixtures of ethylene and butylene midblock copolymer segment of conventional SEBS poly(styrene-ethylene-butylene-styrene) block copolymers is almost totally amorphous, substantially free of any crystallinity or non-crystalline. Such SEBS block copolymers with substantially non-crystalline ethylene-butylene elastomer midblock segment are used for making elastomeric gels of varying rigidities which can vary from soft to firm. Such gels are hereafter referred to as "non-crystalline midblock gels" or "amorphous midblock gels" or more simply "amorphous gels". Generally, the properties of amorphous gels increase with increasing gel rigidity. The amorphous gels at any rigidity, however, can fail catastrophically when cut or notched while under applied forces of high dynamic and static deformations, such as extreme compression, torsion, high tension, high elongation, and the like. Additionally, the development of cracks or crazes resulting from a large number of deformation cycles can induce catastrophic fatigue failure of amorphous gel composites, such as tears and rips between the surfaces of the amorphous gel and substrates or at the interfaces of interlocking material(s) and amorphous gel. Consequently, such amorphous gels made from SEPS and SEBS are inadequate for the most demanding applications involving endurance at high stress and strain levels over an extended period of time.

SUMMARY OF THE INVENTION

I have now discovered novel gels with improved properties made from thermoplastic elastomer copolymers and block copolymers having one or more substantially crystalline polyethylene segment midblocks exhibiting greater advantage over other non-crystalline component forming gels. The crystal gels advantageously exhibit high, higher, and ever higher tear resistances than ever realized before as well as improved high tensile strength.

The advances in improved properties of the crystal gels over amorphous gels are many, these include: improved damage tolerance, improved crack propagation resistance, improved tear resistance, improved resistance to fatigue, etc. Such crystal gels are advantageous for end-use involving repeated applications of stress and strain resulting from large number of cycles of deformations, including compression, compression-extension (elongation), torsion, torsion-compression, torsion-elongation, tension, tension-compression, tension-torsion, etc. The crystal gels also exhibit improved damage tolerance, crack propagation resistance and especially improved resistance to high stress rupture which combination of properties makes the gels advantageously and surprisingly exceptionally more suitable than amorphous gels made from non-crystalline poly(ethylene) component copolymers at corresponding gel rigidities.

The crystal gels which are advantageously useful for making various toys, medical devices, and other useful articles of manufacture including disposable inflatable restraint cushions comprises: 100 parts by weight of one or more high viscosity (I) linear triblock copolymers, (II) multi-arm block copolymers, (III) branched block copolymers, (IV) radial block copolymers, (V) multiblock copolymers, (VI) random copolymers, (VII) thermoplastic crystalline polyurethane copolymers with hydrocarbon midblocks or mixtures of two or more (I)–(VII) copolymers in combination with or without major or minor amounts of one or more other (VIII) copolymers or polymers, said copolymers having one or more segments or one or more midblocks comprising one or more substantially crystalline polyethylene segments or midblocks and selected amounts of a compatible plasticizer (IX) sufficient to achieve gel rigidities of from less than about 2 gram Bloom to about 1,800 gram Bloom with the proviso that when said (I)–(VII) copolymers having nil amorphous segment or nil amorphous midblock are combined with one or more (VIII) copolymers having one or more amorphous segments or amorphous midblocks to form a stable plasticizer compatible gel.

As used herein, the term "gel rigidity" in gram Bloom is determined by the gram weight required to depress a gel a distance of 4 mm with a piston having a cross-sectional area of 1 square centimeter at 23° C.

The gels comprising the thermoplastic elastomer copolymers and block copolymers having one or more substantially crystalline polyethylene segments or midblocks of the invention are hereafter referred to as "elastic-crystalline gels" or simpler "crystal gels". The segments or midblocks of copolymers forming the crystal gels of the invention are characterized by sufficient crystallinity as to exhibit a melting endotherm of at least about 40° C. as determined by DSC curve.

The various types of high viscosity copolymers and block copolymers employed in forming the crystal gels of the invention are of the general configurations (Y-AY)n copolymers, A-Z-A, and (A-Z)n block copolymers, wherein the subscript n is two, three, four, five or more. In the case of multiarm block copolymers where n is 2, the block copolymer denoted by (A-Z)n is A-Z-A. It is understood that the coupling agent is ignored for sake of simplicity in the description of the (A-Z)n block copolymers.

The segment (A) comprises a glassy amorphous polymer end block segment which can be polystyrene, poly(alpha-methylstyrene), poly(o-methylstyrene), poly(m-methylstyrene), poly(p-methylstyrene) and the like, preferably, polystyrene.

The segment (Y) of (VI) copolymers (Y-AY)n comprises substantially crystalline poly(ethylene) (simply denoted by "-E-" or (E)). In the case of (VI) copolymers (A-Y)n, (Y) when next to (A) may be substantially non-crystalline or amorphous ethylene segments. For example a crystalline copolymer (Y-AY)n may be represented by: . . . -E-E-E-E-E-E-E-E-E-SE-E-E-E-E-E-E-SE-E-E-E-E-E-SE- . . . Where Y is a long run of polyethylenes or a non-crystalline copolymer (AY-AY)n: . . . -E-SE-SE-E-SE-E-SE-E-SE-E-E-SE-SE-E-SE- . . . , Where Y is a non-crystalline run of ethylene.

The end block segment (A) comprises a glassy amorphous polymer end block segment which can be polystyrene, poly(alpha-methylstyrene), poly(o-methylstyrene), poly(m-methylstyrene), poly(p-methylstyrene) and the like, preferably, polystyrene. The segment (Y) of (VI) random copolymers A-Y comprises substantially crystalline poly (ethylene) (simply denoted by "-E-" or (E)). In the case of (VIII) random copolymers A-Y, (Y) may be substantially non-crystalline or amorphous ethylene segments. The midblocks (Z) comprises one or more midblocks of substantially crystalline poly(ethylene) (simply denoted by "-E- or (E)") with or without one or more amorphous midblocks of poly(butylene), poly(ethylene-butylene), poly(ethylene-propylene) or combination thereof (the amorphous midblocks are denoted by "-B- or (B)", "-EB- or (EB)", and "-EP- or (EP)" respectively or simply denoted by "-W- or (W)" when referring to one or more of the amorphous midblocks as a group) The A and Z, and A and Y portions are incompatible and form a two or more-phase system consisting of sub-micron amorphous glassy domains (A) interconnected by (Z) or (Y) chains. The glassy domains serve to crosslink and reinforce the structure. This physical elastomeric network structure is reversible, and heating the polymer above the softening point of the glassy domains temporarily disrupt the structure, which can be restored by lowering the temperature. During mixing and heating in the presence of compatible plasticizers, the glassy domains (A) unlock due to both heating and solvation and the molecules are free to move when shear is applied. The disruption and ordering of the glassy domains can be viewed as a unlocking and locking of the elastomeric network structure. At equilibrium, the domain structure or morphology as a function of the (A) and (Z) or (A) and (Y) phases (mesophases) can take the form of spheres, cylinders, lamellae, or bicontinous structures. The scale of separation of the phases are typically of the order of hundreds of angstroms, depending upon molecular weights (i.e. Radii of gyration) of the minority-component segments. At such small domain scales, when the gel is in the molten state while heated and brought into contact to be formed with any substrate and allowed to cool, the glassy domains of the gel become interlocked with the surface the substrate. At sufficiently high enough temperatures, with or without the aid of other glassy resins, the glassy domains of the copolymers forming the gels fusses and interlocks with even a visibly smooth substrate surface such as glass. The disruption of the sub-micron domains due to heating above the softening point forces the glassy domains to open up, unlocking the network structure and flow. Upon cooling below the softing point, the glassy polymers reforms together into sub-micron domains, locking into a network structure once again, resisting flow. It is this unlocking and locking of the network structure on the sub-micron scale with the surfaces of various materials which allows the gel to form interlocking composites with other materials. Such interlocking with many different materials produce gel composites having many uses.

The (I) linear block copolymers are characterized as having a Brookfield Viscosity value at 5 weight percent solids solution in toluene at 30° C. of from less than about 40 cps to about 60 cps and higher, advantageously from about 40 cps to about 160 cps and higher, more advantageously from about 50 cps to about 180 cps and higher, still more advantageously from about 70 cps to about 210 cps and higher, and even more advantageously from about 90 cps to about 380 cps and higher.

The (II, IV, and V) branched, star-shaped (radial), or multiarm block copolymers are characterized as having a Brookfield Viscosity value at 5 weight percent solids solution in toluene at 30° C. of from about 80 cps to about 380 cps and higher, advantageously from about 150 cps to about 260 cps and higher, more advantageously from about 200 cps to about 580 cps and higher, and still more advantageously from about 100 cps to about 800 cps and higher.

The crystal gels can be made in combination with a selected amount of one or more selected polymers and copolymers (II) including thermoplastic crystalline polyurethane elastomers with hydrocarbon blocks, homopolymers, copolymers, block copolymers, polyethylene copolymers, polypropylene copolymers, and the like described below.

The crystal gels of the invention are also suitable in physically interlocking or forming with other selected materials to form composites combinations. The materials are selected from the group consisting of paper, foam, plastic, fabric, metal, metal foil, concrete, wood, glass, various natural and synthetic fibers, including glass fibers, ceramics, synthetic resin, and refractory materials.

The high tear resistant soft crystal gels are advantageously suitable for a safer impact deployable air bag cushions, the higher tear resistant crystal gels are advantageously more suitable, and the highest tear resistant crystal gels are advantageously even more suitable for such use and other uses.

The various aspects and advantages will become apparent to those skilled in the art upon consideration of the accompanying disclosure.

The crystal gels of the invention can be formed into gel strands, gel tapes, gel sheets, and other articles of manufacture in combination with or without other substrates or materials such as natural or synthetic fibers, multifibers, fabrics, films and the like. Moreover, because of their improved tear resistance and resistance to fatigue, the crystal gels exhibit versatility as balloons for medical uses, such as balloon for valvuloplasty of the mitral valve, gastrointestinal balloon dilator, esophageal balloon dilator, dilating balloon catheter use in coronary angiogram and the like. Since the crystal gels are more tear resistant, they are especially useful for making condoms, toy balloons, and surgical and examination gloves. As toy balloons, the crystal gels are safer because it will not rupture or explode when punctured as would latex balloons which often times cause injures or death to children by choking from pieces of latex rubber. The crystal gels are advantageously useful for making gloves, thin gloves for surgery and examination and thicker gloves for vibration damping which prevents damage to blood capillaries in the fingers and hand caused by handling strong shock and vibrating equipment. The crystal gels are also useful for forming orthotics and prosthetic articles such as for lower extremity prosthesis described below.

The EB copolymer midblock of conventional SEBS is almost totally amorphous and the EP midblock of SEPS is amorphous and non-crystalline.

Gels made from such block copolymers are rubbery and exhibit substantially no hysteresis. Their rubbery-ness and lack of hysteresis are due to the amorphous nature of their midblocks. Such gels are hereafter referred to as "non-crystalline gels" or more simply as "amorphous gels".

In general, the overall physical properties of amorphous gels are better at higher gel rigidities. The amorphous gels, however, can fail catastrophically when cut or notched while under applied forces of high dynamic and static deformations, such as extreme compression, torsion, high tension, high elongation, and the like. Additionally, the development of cracks or crazes resulting from a large number of deformation cycles can induce catastrophic fatigue failure of amorphous gel composites, such as tears and rips between the surfaces of the amorphous gel and substrates or at the interfaces of interlocking material(s) and gel. Consequently, such amorphous gels are inadequate for the most demanding applications involving endurance at high stress and strain levels over an extended period of time.

DESCRIPTION OF THE DRAWINGS

FIGS. 1 through 4w. Illustrates composites of the invention.

DESCRIPTION OF THE INVENTION

Figure 2A:
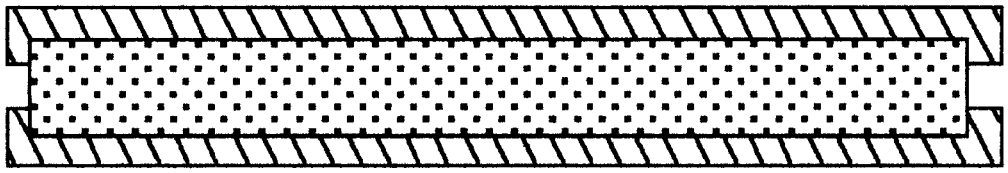
Figure 2B:
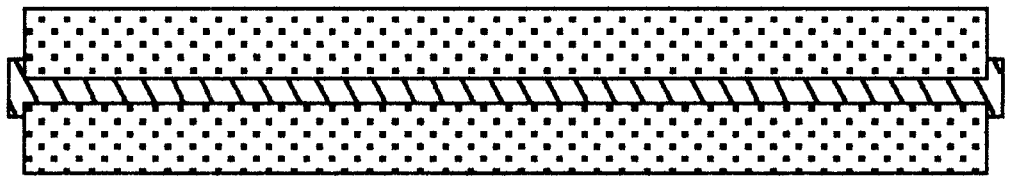
Figure 2C:
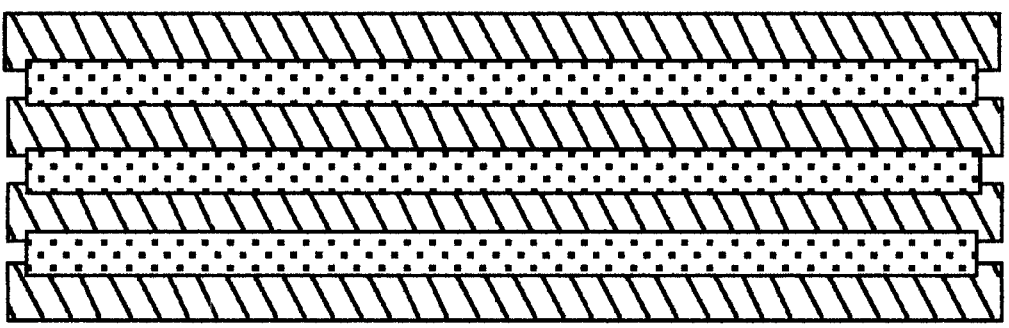
Figure 2D:
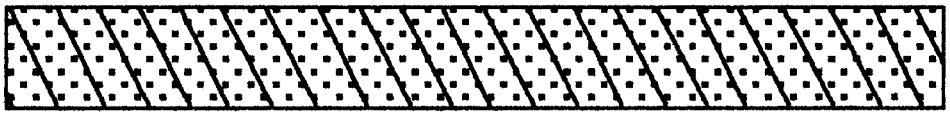
Figure 3A:
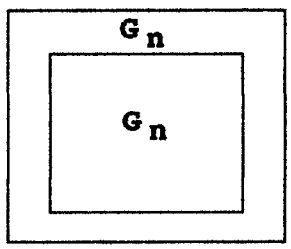
Figure 3B:
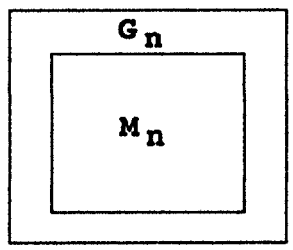
Figure 3C:
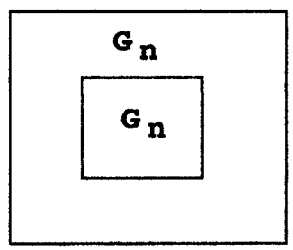
Figure 3D:
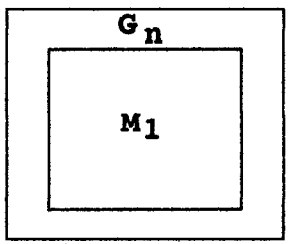
Figure 3E:
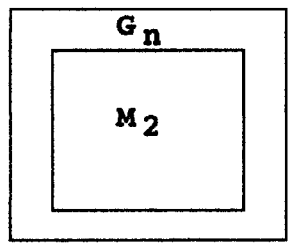
Figure 3F:
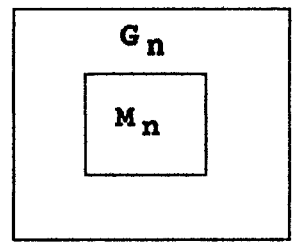
Figure 3G:
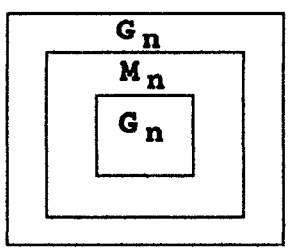
Figure 3H:
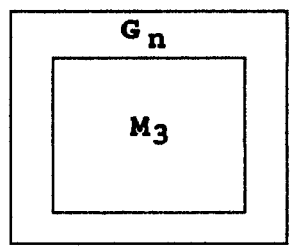
Figure 3I:
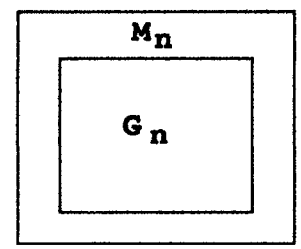
Figure 3J:
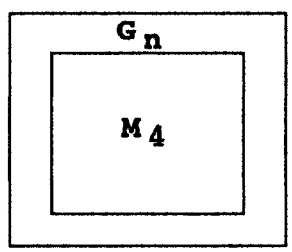
Figure 3K:
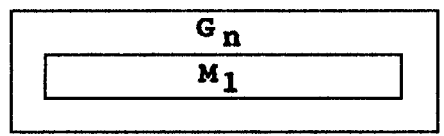
Figure 3L:
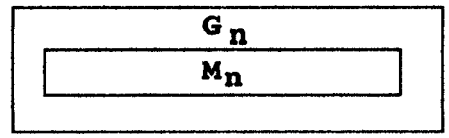
Figure 3M:
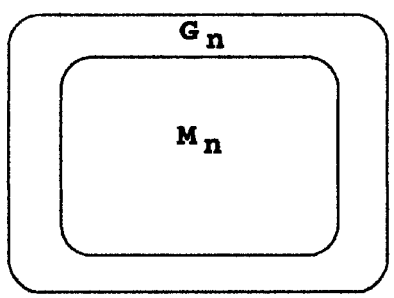
Figure 3N:
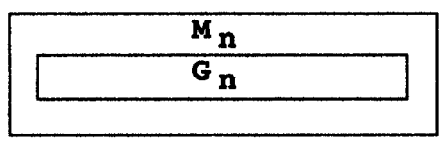
Figure 4A:
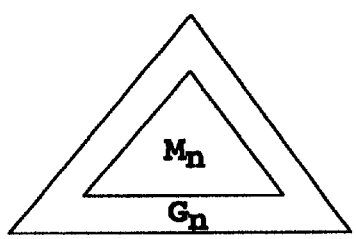
Figure 4B:
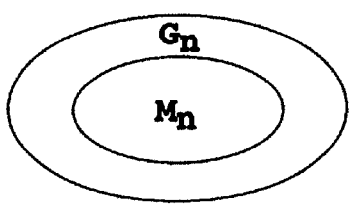
Figure 4C:
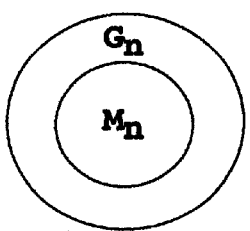
Figure 4D:
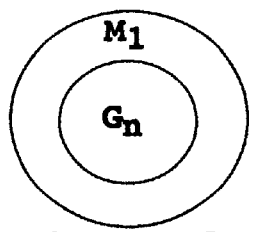
Figure 4E:
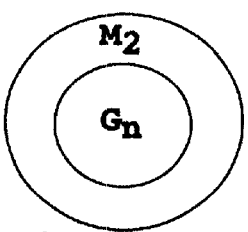
Figure 4F:
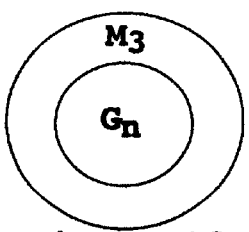
Figure 4G:
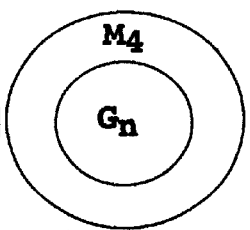
Figure 4H:
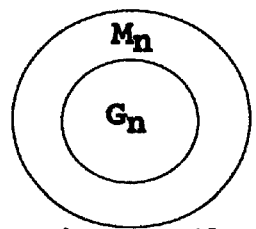
Figure 4I:
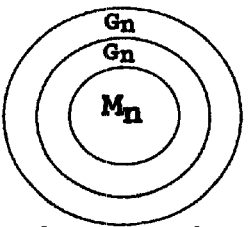
Figure 4J:
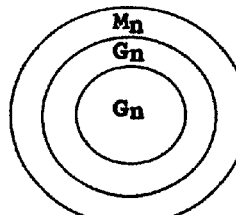
Figure 4K:
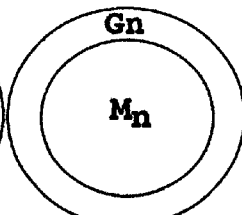
Figure 4L:
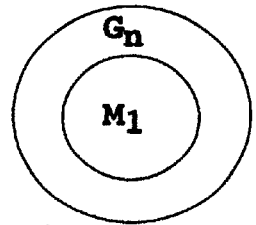
Figure 4M:
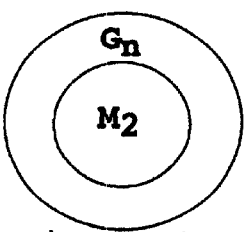
Figure 4N:
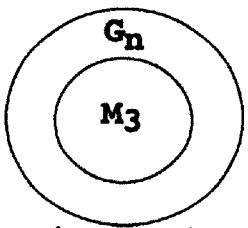
Figure 4O:
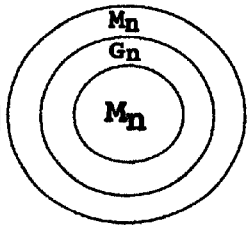
Figure 4P:
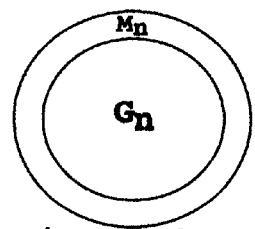
Figure 4Q:
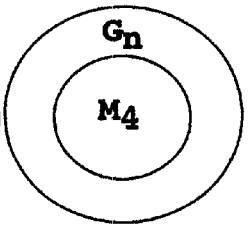
Figure 4R:
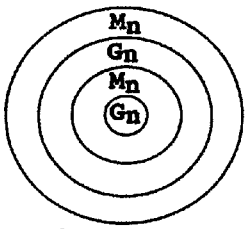
Figure 4S:
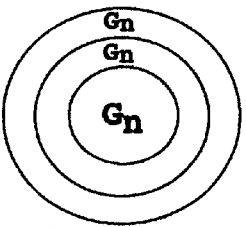
Figure 4T:
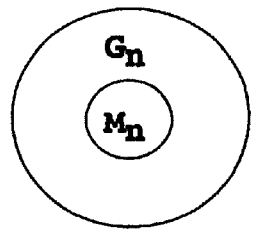
Figure 4U:
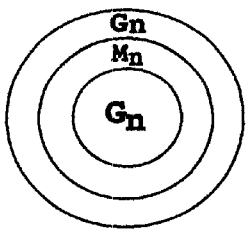
Figure 4V:
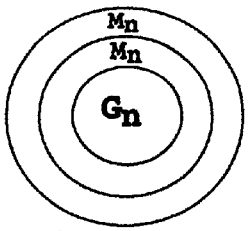
Figure 4W:
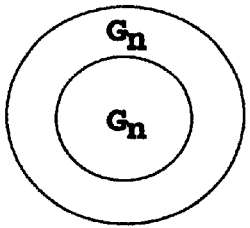

Thermoplastic elastomer SEBS gels are described in my earlier applications and patents: U.S. Ser. Nos.: 581,188 filed Dec. 29, 1995; 581,191 filed Dec. 29, 1995; 581,125 filed Dec. 29, 1995; PCT/US94/04278 filed Apr. 19, 1994; PCT/US94/07314 filed Jun. 27, 1994; Ser. No. 288,690 filed Aug. 11, 1994; Ser. No. 152,734, filed Nov., 15, 1993; Ser. No. 152,735, Nov. 15, 1993; Ser. No. 114.688, filed Aug. 30, 1993; Ser. No. 935,540 filed Aug. 24, 1992; Ser. No. 876,118 filed Apr. 29, 1992; Ser. No. 705,096 filed May 23, 1991; Ser. No. 527,058 filed May 21, 1990; Ser. No. 921,752 filed Oct. 21, 1986; Ser. No. 458,703, filed Jan. 17, 1983; Ser. No. 916,731, filed Jun. 19, 1978; Ser. No. 815,315, filed Jul. 13, 1977; Ser. No. 778,343, filed Mar. 17, 1977; U.S. Pat. Nos. 5,262,468; 5,153,254; 4,618,213; and 4,369,284. Various patents on thermoplastic elastomers and blends are described in U.S. Pat. Nos. 3,595,942, Reissue 27,145-28, 236; U.S. Pat. Nos. 3,772,234; 4,116,917; 4,687,815; and 4,880,878. Other non-patent publications related to S-EB-S polymers include: (1) W. P. Gergen, "Uniqueness of Hydrogenated Block Copolymers for Elastomeric Applications," presented at the German Rubber Meeting, Wiesbaden, 1983; Kautsch, Gummi, Kunstst. 37, 284 (1984). (2) W. P. Gergen, et al., "Hydrogenated Block Copolymers," Paper No. 57, presented at a meeting of the Rubber Division ACS, Los Angeles, Apr. 25, 1985. Encyclopedia of Polymer Science and Engineering, Vol. 2, pp 324–434, "Block Copolymers". (3) L. Zotteri and et al., "Effect of hydrogenation on the elastic properties of poly(styrene-b-diene-b-styrene) copolymers", Polymer, 1978, Vol. 19, April. (4) J. Kenneth Craver, et al., Applied Polymer Science, Ch. 29, "Chemistry and Technology of Block Polymers", pp. 394–429, 1975. (5) Y. Mahajer and et al., "The influence of Molecular Geometry on the Mechanical Properties of homopolymers and Block Polymers of Hydrogenated Butadiene and Isoprene" reported under U.S. ARO Grant No. DAAG29-78-G-0201. (6) J. E. McGrath, et al., "Linear and Star Branched Butadiene-Isoprene Block Copolymers and Their Hydrogenated Derivatives", Chem. Dept, Virginia Polytechnic Institute and State University Blacksturg, Va., reported work supported by Army Research Office. (7) Legge, Norman R., "Thermoplastic Elastomers", Charles Goodyear Medal address given at the 131st Meeting of the Rubber Division, American Chemical Society, Montreal, Quebec, Canada, Vol. 60, G79–G115, May 26–29, 1987. (8) Falk, John Carl, and et al., "Synthesis and Properties of Ethylene-Butylene-1 Block Copolymers", Macromolecules, Vol. 4, No. 2, pp. 152–154, March–April 1971. (9) Morton, Maurice, and et al., "Elastomeric Polydiene ABA Triblock Copolymers within Crystalline End Blocks", University of Arkon, work supported by Grant No. DMR78-09024 from the National Science Foundation and Shell Development Co. (10) Yee, A. F., and et al., "Modification of PS by S-EB-S Block Copolymers: Effect of Block Length", General Electric Corporate Research & Development, Schenectady, N.Y. 12301. (11) Siegfried, D. L., and et al., "Thermoplastic Interpenetrating Polymer Networks of a Triblock Copolymer elastomer and an Monomeric Plastic Mechanical Behavior", Polymer Engineering and Science, January 1981, Vol. 21, No.1, pp 39–46. (12) Clair, D. J., "S-EB-S Copolymers Exhibit Improved Wax Compatibility", Adhesives Age, November, 1988. (13) Shell Chemical Technical Bulletin SC:1102–89, "Kraton® Thermoplastic Rubbers in oil gels", April 1989. (14) Chung P. Park and George P. Clingerman, "Compatibilization of Polyethylene-Polystyrene Blends with Ethylene-Styrene Random Copolymers", the Dow Chemical Company, May 1996. (15) Steve Hoenig, Bob Turley and Bill Van Volkenburgh, "Material Properties and Applications of Ethylene-Styrene Interpolymers", the Dow Chemical Company, September 1996. (16) Y. Wilson Cheung and Martin J. Guest, "Structure, Thermal Transitions and Mechanical Properties of Ethylene/Styrene Copolymers", the Dow Chemical Company, May 1996. (17) Teresa Plumley Karjaia, Y. Wilson Cheung and Martin J. Guest, "Melt Rheology and Processability of Ethylene/Styrene Interpolymers", the Dow Chemical Company, May 1997. The above applications, patents and publications are specifically incorporated herein by reference.

Legge's paper teaches the development of (conventional substantially amorphous elastomer midsegment) SEBS triblock copolymers. In the polymerization of butadiene by alkylithium initiators, 1,4-addition or 1,2-addition polymers, mixtures, can be obtained. In forming styrene butadiene triblock copolymers involving the addition of solvating agents such as ethers just before the final styrene charge is added, any excess of ethers can alter the polybutadiene structure from a 1,4-cis or trans structure to a 1,2- or 3,4-addition polymer. Using difunctional coupling agent would give linear block copolymers and multifuntional agents would give star-shaped or radial block copolymers. Hydrogenation of the 1,4-polybutadiene structure yields polyethylene, while that of the 1,2-polybutadiene yields polybutylene. The resulting polyethylene will be essentially identical with linear, high-density polyethylene with a melting point, Tm, of about 136° C. Hydrogenation of 1,2-polybutadiene would yield atactic poly(1-butene) (polybutylene). The Tg of polybutylene is around −18° C. Random mixtures of ethylene and butylene units in the chain would suppress crystallinity arising from polyethylene sequences. The objective for a good elastomer should be to obtain a saturated olefin elastomeric segment with the lowest possible Tg and the best elastomeric properties. Such an elastomer favored using styrene as the hard-block monomer and selecting the best monomer for hydrogenation of the elastomer midsegment. Using a mixture of 1,4- and 1,2-polybutadiene as the base polymer for the midsegment would result in an ethylene/butylene midsegment in the final product. The elements of selection of the midsegment composition is elastomer crystallinity and the elastomer Tg of an ethylene/butylene copolymer. Very low levels of crystallinity can be achieved around 40–50% butylene concentration. The minimum in dynamic hysteresis around 35% butylene concentration in the elastomeric copolymer. A value of 40% butylene concentration in the ethylene/butylene midsegment was chosen for the S-EB-S block copolymers.

Clair's paper teaches that the EB midblock of conventional S-EB-S polymers is a random copolymer of ethylene and 1-butene exhibiting nearly no crystallinity in the midblock. In the preparation of ethylene-butylene (EB) copolymers, the relative proportions of ethylene and butylene in the EB copolymer chain can be controlled over a broad range from almost all ethylene to almost all butylene. When the EB copolymer is nearly all ethylene, the methylene sequences will crystallize exhibiting properties similar to low density polyethylene. In differential scanning calorimeter (DSC) curves, the melting endotherm is seen on heating and a sharp crystallization exotherm is seen on cooling. As the amount of butylene in the EB copolymer is increased, the methylene sequences are interrupted by the ethyl side chains which shorten the methylene sequences length so as to reduce the amount of crystallinity in the EB copolymer. In conventional S-EB-S polymers, the amount of 1-butene is controlled at a high enough level to make the EB copolymer midblock almost totally amorphous so as to make the copolymer rubbery and soluble in hydrocarbon solvents. Clair suggests that an S-EB-S polymer retaining at least some crystallinity in the EB copolymer midblock may be desirable. Therefore, a new family of S-EB-S polymers are developed (U.S. Pat. No. 3,772,234) in which the midblock contains a higher percentage of ethylene. The molecular weights of the new crystalline midblock segment S-EB-S polymers can vary from low molecular weight, intermediate molecular, to high molecular weight; these are designated Shell GR-3, GR-1, and GR-2 respectively. Unexpectly, the highest molecular weight polymer, GR-2 exhibits an anomalously low softening point. A broad melting endotherm is seen in the DSC curves or these polymers. The maximum in this broad endotherm occurs at about 40° C.

Himes, et al., (U.S. Pat. No. 4,880,878) describes SEBS blends with improved resistance to oil absorption.

Papers (14)–(17) describes poly(ethylene-styrene) random copolymers (Dow Interpolymers™): Dow S, M and E Series produced by metallocene catalysts, using single site, constrained geometry addition polymerization catalysts resulting in poly(ethylene-styrene) random copolymers with weight average molecular weight (Mw) typically in the range of $1 \times 10^5$ to $4 \times 10^5$, and molecular weight distributions (Mw/Mn) in the range of 2 to 3.

The type S series has more than 50 wt % styrene and is glassy at short times and rubbery at long times and exhibits ambient Tg, melt density of about higher than 0.952 to about 0.929 and less, typical Mw=about less than 150,000 to 350,000 and higher.

The type M series has more than 50 wt % styrene is amorphous rubber and exhibits very low modulus, high elasticity, low Tg of from greater than 10° C. to less than −50° C., melt Index of from higher than 5 to less than about 0.1, melt density of higher than 0.93 to 9.0 and less, typical Mw=about less than 200,000 to 300,000 and higher.

The type E series contains up to 50 wt % styrene is semi-crystalline rubber and exhibits low Tg of from greater than 0° C. to about less than −70, low modulus semi-crystalline, good compression set, Melt Index of from about higher than 2 to less than 0.03, melt density of about higher than 0.90 to 0.805 and less, Mw=about less than 250,000 to 350,000 and higher.

The E series random copolymers can be blended with the type M and type S series copolymers and one or more of the I, II, III, IV, V, and VII copolymers to form crystalline polymer gel blends useful for the crystal gels of the invention.

Block copolymers with polyethylene midblocks alone do not form suitable gels for purpose of the invention. Crystalline midblock regions needs to be balanced with amorphous midblock regions in order to obtain soft, flexible and elastic gels with the desired crystalline properties that are not found in totally amorphous gels.

The various representative crystalline/glassy domain/amorphous structures of S-E-EB-S, S-EB45-EP-S, S-E-EB25-S, S-E-EP-E-S, S-EP-E-S and S-EP-E-EP-S. Although the structure are spheroid representation, cylinders and plates are also within the scope of the present invention. Cylinder and plate structure are obtained with increasing glassy A end blocks. From about 15–30% by weight of A blocks, the block copolymer structure is spheroid. From about 33 about 40% by weight of A blocks, the block copolymer structure becomes cylindrical; and above about 45% A blocks, the structure becomes less cylindrical and more plate like.

In order to obtain elastic crystal gels of the invention, it is necessary that the selective synthesis of butadiene produce sufficient amounts of 1,4 poly(butadiene) that on hydrogenation can exhibit "crystallinity" in the midblocks. In order for the block copolymers forming the crystal gels of the invention to exhibit crystallinity, the crystalline midblock segments must contain long runs of —CH2-groups. There should be approximately at least 16 units of —(CH2)- in sequence for crystallinity. Only the (—CH2-)4 units can crystallize, and then only if there are at least 4 units of (—CH2-)4 in sequence; alternatively, the polyethylene units are denoted by [—CH2-CH2-CH2-CH2)-]4, [(—CH2-)4]or (—CH2-)16. The amount of (—CH2-)16 units forming the (E) midblocks of the block copolymers comprising the crystal gels of the invention should be at least about 20% which amount is capable of exhibiting a melting endotherm in differential scanning calorimeter (DSC) curves.

Advantageously, the elastomer midblock segment should have a crystallinity of at least about 20% of (—CH2-)16 units of the total mole % forming the midblocks of the block copolymer, more advantageously at least about 25%, still more advantageously at least about 30%, especially advantageously at least about 40% and especially more advantageously at least about 50% and higher. Broadly, the crystallinity of the midblocks should range from at least about 20% to about 60%, less broadly from at least about 18% to about 65%, and still less broadly from at least 22% to about 70%.

The melting endotherm in DSC curves of the crystalline block copolymers comprising at least 20% crystallinity are much higher than conventional amorphous block copolymers. The maximum in the endotherm curves of the crystalline block copolymers occurs at about 40° C., but can range from greater than about 25° C. to about 60° C. and higher. The crystalline block copolymers forming the crystal gels of the invention can exhibit melting endotherms (as shown by DSC) of about 25° C. to about 75° C. and higher. More specific melting endotherm values of the crystalline midblock block copolymers include: about 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 90° C., 100° C., 110° C., 120° C., and higher whereas, the melting endotherm (DSC) for conventional amorphous midblock segment block copolymers are about 10° C. and lower.

The melting endotherm is seen on heating and a sharp crystallization exotherm is seen on cooling. Such midblock crystallization endothermic and exothermic characteristics are missing from DCS curves of amorphous gels. The crystallization exotherm and fusion endortherm of the crystalline block copolymer gels of the invention are determined by ASTM D 3417 method.

Generally, the method of obtaining long runs of crystalline —(CH2)- is by sequential block copolymer synthesis followed by hydrogenation. The attainment of crystal gels of the instant invention is solely due to the selective polymerization of the butadiene monomer (forming the midblocks) resulting in one or more predetermined amount of 1,4 poly(butadiene) blocks followed by sequential polymerization of additional midblocks and hydrogenation to produce one or more crystalline midblocks of the final block copolymers.

The crystalline block copolymers are made by sequential block copolymer synthesis, the percentage of crystallinity or (—CH2-)16 units should be at least about $(0.67)^4$ or about 20% and actual crystallinity of about 12%. For example, a selectively synthesized S-EBn-S copolymer having a ratio of 33:67 of 1,2 and 1,4 poly(butadiene) on hydrogenation will result in a midblock with a crystallinity of $(0.67)^4$ or 20%. For sake of simplicity, when n is a subscript of -EB-, n denotes the percentage of (—CH2-)4 units, eg, n=33 or 20% crystallinity which is the percentage of $(0.67)^4$ or "$(—CH_2—)_{16}$" units. Thus, when n=28 or 72% of $(—CH_2—)_4$ units the % crystallinity is $(0.72)^4$ or 26.87% crystallinity attributed to $(—CH_2—)_{16}$ units, denoted by -EB$_{28}$—. As a matter of convention, and for purposes of this specification involving hydrogenated polybutadiene: the notation -E- denotes at least about 85% of (—CH$_2$—)$_4$ units. The notation -B- denotes at least about 70% of [—CH$_2$—CH(C$_2$H$_5$)—] units. The notation -EB- denotes between about 15 and 70% [—CH$_2$—CH(C$_2$H$_5$)—] units. The notation -EB$_n$- denotes n % [—CH$_2$—CH(C$_2$H$_5$)—] units. For hydrogenated polyisoprene: The notation -EP- denotes about at least 90% [—CH$_2$—CH(CH$_3$)—CH$_2$—CH$_2$—] unit.

Generally, one or more (E) midblocks can be incorporated at various positions along the midblocks of the block copolymers. Using the sequential process for block copolymer synthesis, The (E) midblocks can be positioned as follows:
i) A-E-W-A
ii) A-E-W-E-A
ii) A-W-E-W-A
iii) A-E-W-E-W-E-W-E-A
iv) A-W-E-W-A-E-A-E-W-E-A
v) and etc.

The lower flexibility of block copolymer crystal gels due to (E) midblocks can be balanced by the addition of sequentially (W) midblocks. For example, the sequentially synthesized block copolymer S-E-EB-S can maintain a high degree of flexibility due to the presence of amorphous -EB- block. The sequential block copolymer S-E-EB-B-S can maintain a high degree of flexibility due to the presence of amorphous -EB- and -B- midblocks. The sequential block copolymer S-E-EP-E-S can maintain a high degree of flexibility due to the presence of -EP- midblock. The sequential block copolymer S-E-B-S can maintain a high degree of flexibility due to the presence of the -B- midblock. For S-E-S, where the midblock is substantially crystalline and flexibility low, physical blending with amorphous block copolymers such as S-EB-S, S-B-S, S-EP-S, S-EB-EP-S, (S-EP)n and the like can produce more softer, less rigid, and more flexible crystal gel.

Because of the (E) midblocks, the crystal gels of the invention exhibit different physical characteristics and improvements over substantially amorphous gels including damage tolerance, improved crack propagation resistance, improved tear resistance producing knotty tears as opposed to smooth tears, crystalline melting point of at least 28° C., improved resistance to fatigue, higher hysteresis, etc. Moreover, the crystal gels when stretched exhibit additional yielding as shown by necking caused by stress induced crystallinity. Additionally, the crystallization rates of the crystalline midblocks can be controlled and slowed depending on thermal history producing time delay recovery upon deformation.

Regarding resistance to fatigue, fatigue (as used herein) is the decay of mechanical properties after repeated application of stress and strain. Fatigue tests give information about the ability of a material to resist the development of cracks or crazes resulting from a large number of deformation cycles. Fatigue test can be conducted by subjecting samples of amorphous and crystal gels to deformation cycles to failure (appearance of cracks, crazes, rips or tears in the gels).

Tensile strength can be determined by extending a selected gel sample to break as measured at 180° U bend around a 5.0 mm mandrel attached to a spring scale. Likewise, tear strength of a notched sample can be determined by propagating a tear as measured at 180° U bend around a 5.0 mm diameter mandrel attached to a spring scale.

Various block copolymers can be obtained which are amorphous, highly rubbery, and exhibiting minimum dynamic hysteresis:

Block Copolymer S-EB-S

The monomer butadiene can be polymerized in a ether/hydrocarbon solvent to give a 50/50 ratio of 1,2 poly (butadiene)/1,4 poly(butadiene) and on hydrogenation no long runs of —CH2-groups and negligible crystallinity, ie, about $(0.5)^4$ or 0.06 or 6% and actual crystallinity of about 3%. Due to the constraints of Tg and minimum hysteresis, conventional S-EB-S have ethylene-butylene ratios of about 60:40 with a crystallinity of about $(0.6)^4$ or 0.129 or 12% and actual crystallinity of about 7.7%.

Block Copolymer S-EP-S

The monomer isoprene when polymerized will produce 95% 1,4 poly(isoprene)/5% 3,4 poly(isoprene) and upon hydrogenation will form amorphous, rubbery poly(ethylene-propylene) midblock and no long runs of —CH2- and no crystallinity.

Mixed Block Copolymer S-EB/EP-S

The polymerization of a 50/50 mixture of isoprene/butadiene monomers in suitable ether/hydrocarbon solvents to give equal amounts of 1,2 and 1,4 poly(butadiene) on hydrogenation will produce a maximum crystallinity of $(0.25)^4$ or 0.4%. The actual crystallinity would be approximately about 0.2%, which is negligible and results in a good rubbery midblock.

The polymerization of a 80/20 mixture of isoprene/butadiene monomers in suitable ether/hydrocarbon solvents to give equal amounts of 1,2 and 1,4 poly(butadiene) will upon hydrogenation produce a low crystallinity of $(0.10)^4$ or 0.01%. The actual crystallinity would be approximately about 0.006%, which is negligible and results in a good rubbery midblock.

The polymerization of a 20/80 mixture of isoprene/butadiene monomers in suitable ether/hydrocarbon solvents to give equal amounts of 1,2 and 1,4 poly(butadiene) will upon hydrogenation produce a low crystallinity of $(0.4)^4$ or 2.56%. The actual crystallinity would be approximately about 1.53%, which is negligible and results in a good rubbery midblock.

The polymerization of a 20/80 mixture of isoprene/butadiene monomers in suitable ether/hydrocarbon solvents to give a 40:60 ratio of 1,2 and 1,4 poly(butadiene) will upon hydrogenation produce a low crystallinity of $(0.48)4$ or 5.3%. The actual crystallinity would be approximately about 3.2%, which is negligible and results in a good rubbery midblock.

For purpose of convince and simplicity, the hydrogenated polybutadiene are denoted as follows: E-denotes at least 85% R-1 units, -B- denotes at least 70% R-2 units, -EB- denotes between 15 and 70% R-2 units, -EBn- denotes n % R-2 units, and -EP- denotes 90% R-3 units.

Table I below gives the % of units on hydrogenation of polybutadiene/polyisoprene copolymer midblocks

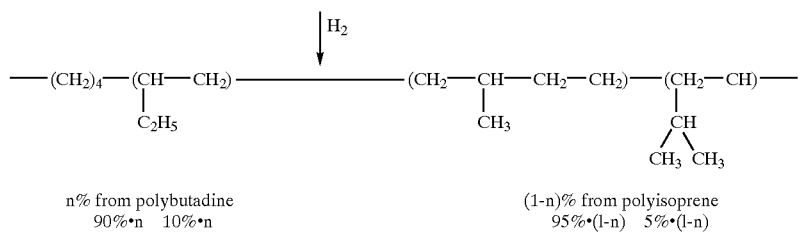

n% from polybutadine
90%•n   10%•n (1-n)% from polyisoprene
95%•(1-n)   5%•(1-n)

where n is the mole % polybutadiene in the polybutadiene-polyisoprene starting polymer

| n = | R-1 | R-2 | R-3 | R-4 |
|---|---|---|---|---|
| 0% | 0% | 0% | 95% | 5% |
| 20% | 18% | 2% | 76% | 4% |
| 40% | 36% | 4% | 57% | 3% |
| 60% | 54% | 6% | 38% | 2% |
| 80% | 72% | 8% | 19% | 1% |
| 100% | 90% | 10% | 0% | 0% | where R-1 denotes $(-CH_2-)_4$,

R-2 denotes 
$$-(CH-CH_2)-$$
     $|$
     $C_2H_5$

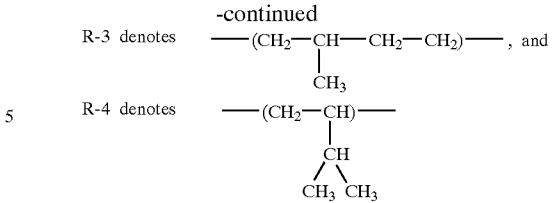

Therefore, the percentage that can crystallize is $\sim[(-CH_2-)_4]_4$ since this is the chance of getting four $(-CH_2-)_4$ units in sequence.

| n = | $(-CH_2-)_4$ | $[(-CH_2-)_4]_4$ | $0.6 \times [(-CH_2-)_4]_n$ |
|---|---|---|---|
| 0% | 0% | 0% | 0% |
| 20% | 18% | 0.1% | 0.06% |
| 40% | 36% | 1.7% | 1.0% |
| 60% | 54% | 8.5% | 5.1% |
| 80% | 72% | 26.9% | 16.1% |
| 100% | 90% | 65.6% | 39.4% |

This applies to polymerization in a hydrocarbon solvent. In an ether eg, diethylether), the percentage ($-CH2-$)4 units will be reduced so that crystallinity will be negligible.

| n = | $(-CH_2-)_4$ | $[(-CH_2-)_4]_4$ | $0.6 \times [(-CH_2-)_4]_n$ |
|---|---|---|---|
| 0% | 0% | 0% | 0% |
| 20% | 5% | 0.0006% | 0.0004% |
| 40% | 10% | 0.01% | 0.006% |
| 60% | 15% | 0.05% | 0.03% |
| 80% | 20% | 0.16% | 0.10% |
| 100% | 25% | 0.39% | 0.23% |

These values are all negligible. There will be no detectable crystallinity in any of these polymer midblocks. In a mixed ether/hydrocarbon solvent, values will be intermediate, depending on the ratio of ether to hydrocarbon.

The midblocks (Z) of one or more -E-, -B-, -EB-, or -EP- can comprise various combinations of midblocks between the selected end blocks (A); these include: -E-EB-, -E-EP-, -B-EP-, -B-EB-, -E-EP-E-, -E-EB-B-, -B-EP-B-, -B-EB-B-, -E-B-EB-, -E-B-EP-, -EB-EP-, -E-EB-EP-, -E-EP-EB-, -B-EB-EP-, -B-EP-EB-, -E-EP-E-EP-, -E-EP-E-EB-, -B-EP-B-EP-, -B-EB-B-EB-, -E-EB-B-EB-, -E-EB-B-EP-, -E-EP-B-EB-, -E-EP-E-EP-E-, -B-EP-B-EP-B-, -E-EP-E-

EB-, -E-EP-E-EP-EB-, -E-EP-E-EP-E-, -E-EP-EB-EP-EB-B- and the like.

The block copolymers of (A-Z-A) can be obtained by sequential synthesis methods followed by hydrogenation of the midblocks. As denoted above, abbreviations are interchangeably used, for example, (S-E-EP-S) denotes poly(styrene-ethylene-ethylene-co-propylene-styrene). Other linear block copolymers (denoted in abbreviations) include the following: (S-E-EB-S), (S-E-EP-S), (S-B-EP-S), (S-B-EB-S), (S-E-EP-E-S), (S-E-EB-B-S), (S-B-EP-B-S), (S-B-EB-B-S), (S-E-B-EB-S), (S-E-B-EP-S), (S-EB-EP-S), (S-E-EB-EP-S), (S-E-EP-EB-S), (S-B-EB-EP-S), (S-B-EP-EB-S), (S-E-EP-E-EP-S), (S-E-EP-E-EB-S), (S-EP-B-EP-S), (S-B-EB-B-EB-S), (S-B-EB-B-EP-S), (S-E-EB-B-EP-S), (S-E-EP-B-EB-S), (S-E-EP-E-BP-E-S), (S-EP-EP-B-9), (S-E-EP-E-EB-S), (S-E-EP-E-EP-EB-S), (S-E-EP-E-EP-E-S), (S-E-EP-EB-EP-EB-B-S), (S-E-EP-EB-EP-EB . . . -S) and the like.

The multiblock star-shaped (or radial) copolymers (A-Z)nX can be obtained by sequential synthesis methods including hydrogenation of selected block copolymers made by polymerizing half of the block copolymers such as SBS or SIS and couple the halves with a coupling agent such as an organic dihalide; or couple with an agent such as SnCl4, which results in star-shaped block copolymers (four branches). Coupling with divinyl benzene give block copolymers which are very highly branched. Radial block copolymers suitable for use in forming the crystal gels of the present invention include: (S-E-EB-S)n, (S-E-EP)n, (S-B-EP)n, (S-B-EB)n, (S-E-EP-E)n, (S-E-EB-B)n, (S-B-EP-B)n, (S-B-EB-B)n, (S-E-B-EB)n, (S-E-B-EP)n, (S-EB-EP)n, (S-E-EB-EP)n, (S-E-EP-EB)n, (S-B-EB-EP)n, (S-B-EP-EB)n, (S-E-EP-E-EP)n, (S-E-EP-E-EB)n, (S-EP-B-EP)n, (S-B-EB-B-EB)n, (S-B-EB-B-EP)n, (S-E-EB-B-EP)n, (S-E-EP-B-EB)n, (S-E-EP-E-EP-E)n, (S-B-EP-B-EP-B)n, (S-E-EP-E-EB)n, (S-E-EP-E-EP-EB)n, (S-E-EP-E-EP-E)n, (S-E-EP-EB-EP-EB-B)n The selected amount of crystallinity in the midblock should be sufficient to achieve improvements in one or more physical properties including improved damage tolerance, improved crack propagation resistance, improved tear resistance, improved resistance to fatigue of the bulk gel and resistance to catastrophic fatigue failure of crystal gel composites, such as between the surfaces of the crystal gel and substrate or at the interfaces of the interlocking material(s) and crystal gel, which improvements are not found in amorphous gels at corresponding gel rigidities.

As an example, when fabric interlocked or saturated with amorphous S-EB-S gels (gel composites) are used as gel liners for lower limb or above the knee prosthesis to reduce pain over pressure areas and give relief to the amputee, the commonly used amorphous gels forming the liners can tear or rip apart during marathon racewalk after 50–70 miles. In extended use, the amorphous gels can rip on the bottom of the liner in normal racewalk training of 40–60 miles over a six weeks period. In such demanding applications, the crystal gels are especially advantageous and is found to have greater tear resistance and resistance to fatigue resulting from a large number of deformation cycles than amorphous gels. The crystal gels are also useful for forming various orthotics and prosthetic articles such as for lower extremity prosthesis of the L5664 (lower extremity socket insert, above knee), L5665 (socket insert, multi-durometer, below knee), L5666 (below knee, cuff suspension interface), L5667 (below knee, above knee, socket insert, suction suspension with locking mechanism) type devices as described by the American Orthotic & Prosthetic Association (AOPA) codes. The crystal gels are useful for making AOPA code devices for upper extremity prosthetics. The devices can be cast molded or injection molded in combination with or without fiber or fabric backing or fiber or fabric reinforcement.

Selected (I) linear block and radial copolymers utilized in forming the crystal gels of the invention are characterized as having an ethylene to butylene midblock ratio (E:B) of about 85:15 to about 65:35. Advantageously, the butylene concentration of the midblock is about 35% or less, more advantageously, about 30% or less, still more advantageously, about 25% or less, especially advantageously, about 20% or less. Advantageously, the ethylene to butylene midblock ratios can range from about 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34 to about 65:35.

The A to Z midblock ratio of the block copolymers suitable for forming crystal gels of the invention can range from about 20:80 to 40:60 and higher. More specifically, the values can be 15:85, 19:81, 20:80, 21:79. 22:78. 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and 52:48.

The crystal gels can optionally comprise selected major or minor amounts of one or more polymers or copolymers (II) provided the amounts and combinations are selected without substantially decreasing the desired properties. The polymers and copolymers can be linear, star-shaped (radial), branched, or multiarm; these including: (SBS) styrene-butadiene- styrene block copolymers, (SIS) styrene-isoprene-styrene block copolymers, low and medium viscosity (S-EB-S) styrene-ethylene-butylene-styrene block copolymers, (S-EP) styrene-ethylene-propylene block copolymers, (S-EP-S) styrene-ethylene/propylene-styrene block copolymers, (S-E-EPS) styrene-ethylene-ethylene/propylene-styrene block copolymers, (SB)n styrene-butadiene and (S-EB)n, (S-EB-S)n, (S-E-EP)n, (SEP)n, (SI)n multi-arm, branched or star-shaped copolymers, polyethyleneoxide (EO), poly(dimethylphenylene oxide), teflon (TFE, PTFE, PEA, FEP, etc), optical clear amorphous copolymers based on 2,2-bistrifluoromethyl-4,5-difuoro-1, 3-dioxole (PDD) and tetrafluoroethylene (TFE), maleated S-EB-S block copolymer, polycarbonate, ethylene vinyl alcohol copolymer, and the like. Still, other (II) polymers include homopolymers which can be utilized in minor amounts; these include: polystyrene, polydimethylsiloxane, polyolefins such as polybutylene, polyethylene, polyethylene copolymers, polypropylene,and the like. Polyurethane elastomers based on saturated hydrocarbon diols (Handlin, D., Chin. S., and Masse. M., et al. "POLYURETHANE ELASTOMERS BASED ON NEW SATURATED HYDROCARBON DIOLS" Published Society of Plastics Industry, Polyurethane Division, Las Vegas, Oct. 23, 1996) are also suitable for use in blending with the block copolymers (I) used in forming the crystal gels of the invention. Such saturated hydrocarbon diols include hydroxyl terminated oligomers of poly(ethylene-butylene) (EB), poly(ethylene-propylene) (EP),-E-EB-, -E-EP-, -B-EP-, -B-EB-, -E-EP-E, -E-EB-B-, -B-EP-B-, -B-EB-B-, -E-B-EB-, -E-B-EP-, -EB-EP-, -E-EB-EP-, -E-EP-EB-, -B-EB-EP-, -B-EP-EB-, -E-EP-E-EP-, -E-EP-E-EB -, -B-EP-B-EP-, -B-EB-B-EB-, -B-EB-B-EP-, -E-EB-B-EP-, -E-EP-B-EB-, -E-EP-E-EP-E-, -B-EP-B-EP-B-, -E-EP-E-EB -, -E-EP-E-EP-EB-, -E-EP-E-EP-E-, -E-EP-EB-EP-EB-B- and the like. As an example, thermoplastic polyurethane made with isocyanates and chain extenders such as TMPD and BEPD from saturated hydrocarbon diol KLP L-2203 having a hard segment contents of 22% exhibits clean phase separation of the hard and soft segments with glass a transition of −50° C. KLP L-2203 based TPU's can be mixed with the crystalline block copolymers to form soft crystal gels within the gel rigidity ranges of the invention.

Suitable polyolefins include polyethylene and polyethylene copolymers such as Dow Chemical Company's Dowlex 3010, 2021D, 2038, 2042A, 2049, 2049A, 2071, 2077, 2244A, 2267A; Dow Affinity ethylene alpha-olefin resin PL-1840, SE-1400, SM-1300; more suitably: Dow Elite 5100, 5110, 5200, 5400, Primacor 141—XT, 1430, 1420, 1320, 3330, 3150, 2912, 3340, 3460; Dow Attane (ultra low density ethylene-octene-1 copolymers) 4803, 4801, 4602.

The conventional term "major" means about 51 weight percent and higher (e.g. 55%, 60%, 65%, 70%, 75%, 80% and the like) and the term "minor" means 49 weight percent and lower (e.g. 2%, 5%, 10%, 15%, 20%, 25% and the like).

Example of (II) polymers, copolymers, and blends include: (a) Kraton G 1651, G 1654X; (b) Kraton G 4600; (c) Kraton G 4609; other suitable high viscosity polymer and oils include: (d) Tuftec H 1051; (e) Tuftec H 1041; (f) Tuftec H 1052; (g) Kuraray SEPS 4033; (h) Kuraray S-EB-S 8006; (i) Kuraray SEPS 2005; (0) Kuraray SEPS 2006, and (k) blends (polyblends) of (a)–(h) with other polymers and copolymers include: (1) S-EB-S/SBS; (2) S-EB-S/SIS; (3) S-EB-S/(SEP); (4) S-EB-S/(SEB)n; (5) S-EB-S/(SEB)n; (6) S-EB-S/(SEP)n; (7) S-EB-S/(SI)n; (8) S-EB-S/(SI) multi-arm; (9) S-EB-S/(SEB)n; (10) (SEB)n star-shaped copolymer; (11) s made from blends of (a)–(k) with other homopolymers include: (12) S-EB-S/polystyrene; (13) S-EB-S/polybutylene; (14) S-EB-S/poly-ethylene; (14) S-EB-S/polypropylene; (16) SEP/S-EB-S, (17) SEP/SEPS, (18) SEP/SEPS/SEB, (19), SEPS/S-EB-S/SEP, (20), SEB/S-EB-S (21), EB-EP/S-EB-S (22), S-EB-S/EB (23), S-EB-S/EP (24), (25) (SEB)n s, (26) (SEP)n, (27) Kuraray 2007 (SEPS), (28) Kuraray 2002, (SEPS), (29) Kuraray 4055 (S-EB-EP-S) (30) Kuraray 4077 (S-EB-EP-S) (31) Kuraray 4045 (S-EB-EP-S) (32) (S-EB-EP)n, (33) (SEB)n, (34) EPDM, (35) EPR, (36) EVA, (37) coPP, (38) EMA, (39) EEA, (40) DuPont Teflon AF amorphous fluoropolymers, (41) Dow polydimethylsiloxane, (42) maleated S-EB-S (maleation level 2–30%), (43) (EP)n and the like.

Septon 4033 (SEEPS), 4045 (SEEPS), 4055 (SEEPS), and 4077 (SEEPS) are made from hydrogenated styrene isoprene/butadiene block copolymers, more specifically from hydrogenated styrene block polymer with 2-methyl-1, 3-butadiene and 1,3-butadiene.

Representative examples of commercial elastomers that can be combined with the block copolymers (I) described above include: Shell Kratons D1101, D1102, D1107, D1111, D1112, D1113X, D1114X, D1116, D1117, D1118X, D1122X, D1125X, D1133X, D1135X, D1184, D1188X, D1300X, D1320X, D4122, D4141, D4158, D4240, G1650, G1652, G1657, G1701X, G1702X, G1726X, G1750X, G1765X, FG1901X, FG1921X, D2103, D2109, D2122X, D3202, D3204, D3226, D5298, D5999X, D7340, G1650, G1651, G1652, G4609, G4600, G1654X, G2701, G2703, G2705, G1706, G2721X, G7155, G7430, G7450, G7523X, G7528X, G7680, G7705, G7702X, G7720, G7722X, G7820, G7821X, G7827, G7890X, G7940, FG1901X and FG1921X. Kuraray's SEP, SEPS, S-EB-S, S-EB-EP-S Nos. 1001, 1050, 2027, 2003, 2006, 2007, 2008, 2023, 2043, 2063, 2050, 2103, 2104, 2105, 4033 (SEEPS), 4045 (SEEPS with styrene content of 37.6), 4055 (SEEPS), 4077 (SEEPS), 8004, 8006, 8007, H-VS-3 (S-V-EP)n, and the like.

The amorphous S-EB-S and (S-EB)n (II) copolymers can have a broad range of styrene to ethylene-butylene ratios (S:EB) of about 20:80 or less to about 40:60 or higher. The S:EB weight ratios can range from lower than about 20:80 to above about 40:60 and higher. More specifically, the values can be 15:85, 19:81, 20:80, 21:79. 22:78. 23:77, 24:76, 25:75, 26:74, 27:73, 28:72, 29:71, 30:70, 31:69, 32:68, 33:67, 34:66, 35:65, 36:64, 37:63, 37.6:62.4, 38:62, 39:61, 40:60, 41:59, 42:58, 43:57, 44:65, 45:55, 46:54, 47:53, 48:52, 49:51, 50:50, 51:49 52:48 and etc. Other ratio values of less than 19:81 or higher than 51:49 are also possible. Broadly, the styrene block to elastomeric block ratio of the high viscosity liner and star copolymers is about 20:80 to about 40:60 or higher, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and still more preferably about 30:70.

The Brookfield Viscosity of a 5 weight percent solids solution in toluene at 30° C. of 2006, 4045, 4055, 4077 typically range about 20–35, about 25–150, about 60–150, about 200–400 respect Brookfield Viscosities of a 10 weight percent solids solution in toluene at 30° C. of 1001, 1050, 2007, 2063, 2043, 4033, 2005, 2006, are about 70, 70, 17, 29, 32, 50, 1200, and 1220 respectively. Typical Brookfield Viscosity of a 25 weight percent solids solution in toluene at 25° C. of Kraton D1101, D1116, D1184, D1300X, G1701X, G1702X are about 4000, 9000, 20000, 6000, 50000 and 50000 cps respectively. Typical Brookfield Viscosity of a 10 weight percent solids solution in toluene at 25° C. of G1654X is about 370 cps. The Brookfield Viscosities of a 20 and 30 weight percent solids solution in toluene at 30° C. of H-VS-3 are about 133 cps and 350 cps respectively.

Suitable block copolymers (II) and their typical viscosities are further described. Shell Technical Bulletin SC: 1393-92 gives solution viscosity as measured with a Brookfield model RVT viscometer at 25° C. for Kraton G 1654X at 10% weight in toluene of approximately 400 cps and at 15% weight in toluene of approximately 5,600 cps. Shell publication SC:68–79 gives solution viscosity at 25° C. for Kraton G 1651 at 20 weight percent in toluene of approximately 2,000 cps. When measured at 5 weight percent solution in toluene at 30° C., the solution viscosity of Kraton G 1651 is about 40. Examples of high viscosity S-EB-S triblock copolymers includes Kuraray's S-EB-S 8006 which exhibits a solution viscosity at 5 weight percent at 30° C. of about 51 cps. Kuraray's 2006 SEPS polymer exhibits a viscosity at 20 weight percent solution in toluene at 30° C. of about 78,000 cps, at 5 weight percent of about 27 cps, at 10 weight percent of about 1220 cps, and at 20 weight percent 78,000 cps. Kuraray SEPS 2005 polymer exhibits a viscosity at 5 weight percent solution in toluene at 30° C. of about 28 cps, at 10 weight percent of about 1200 cps, and at 20 weight percent 76,000 cps. Other grades of S-EB-S, SEPS, (SEB)n, (SEP)n polymers can also be utilized in the present invention provided such polymers exhibits the required high viscosity. Such S-EB-S polymers include (high viscosity) Kraton & 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene (S:EB) weight ratios for the Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. In the case of Kuraray's S-EB-S polymer 8006 the S:EB weight ratio is about 35:65. In the case of Kuraray's 2005 (SEPS), and 2006 (SEPS), the S:EP weight ratios are 20:80 and 35:65 respectively. The styrene to ethylene-ethylene/propylene (S:E-EP) ratios of Kuraray's SEPTON 4045, 0455, and 4077 are typically about 37.6, 30, 30 respectively. More typically the (S:EB-EP) and (S:EP) ratios can vary broadly much like S:EB ratios of S-EB-S and (SEB)n from less than 19:81 to higher than 51:49 (as recited above) are possible. It should be noted that multiblock copolymers including SEPTON 4045, 4055, 4077 and the like are described in my cited copending parent applications and are the subject matter of related inventions.

The block copolymers (II) such as Kraton G 1654X having ratios of 31:69 or higher can be used and do exhibit about the same physical properties in many respects to Kraton G 1651 while Kraton G 1654X with ratios below 31:69 may also be use, but they are less advantageous due to their decrease in the desirable properties of the final gel.

Plasticizers (III) particularly advantageous for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

Examples of representative commercially available plasticizing oils include Amoco® polybutenes, hydrogenated polybutenes, polybutenes with epoxide functionality at one end of the polybutene polymer, liquid poly(ethylene/butylene), liquid hetero-telechelic polymers of poly(ethylene/butylene/styrene) with epoxidized polyisoprene and poly(ethylene/butylene) with epoxidized polyisoprene: Example of such polybutenes include: L-14 (320 Mn), L-50 (420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27–37 cst @ 100° F. Viscosity), H-300E (635–690 cst @ 210° F. Viscosity), Actipol E6 (365 Mn), E16 (973 Mn), E23 (1433 Mn), Kraton L-2203 and Kraton L-1203, EKP-206, EKP-207, HPVM-2203 and the like. Example of various commercially oils include: ARCO Prime (55,70,90,200, 350, 400 and the like), Duroprime and Tufflo oils (6006, 6016, 6016M, 6026, 6036, 6056, 6206, etc), other white mineral oils include: Bayol, Bernol, American, Blandol, Drakeol, Ervol, Gloria, Kaydol, Litetek, Lyondell (Duraprime 55, 70, 90, 200, 350, 400, etc), Marcol, Parol, Peneteck, Primol, Protol, Sontex, Witco brand white oils including RR-654-P and the like. Generally, plasticizing oils with average molecular weights less than about 200 and greater than about 700 may also be used (e.g., H-300 (1290 Mn)).

Comparisons of oil extended S-EB-S triblock copolymers have been described in Shell Chemical Company Technical Bulletin SC:1102–89 (April 1989) "KRATON® THERMOPLASTIC RUBBERS IN OIL GELS" which is incorporated herein by reference.

The crystal gels can be made non-adhearing, non-sticking, (non-tacky), by incorporating an advantage amount of stearic acid (octadecanoic acid), metal stearates (e.g., calcium stearate, magnesium stearate, zinc stearate, etc.), polyethylene glycol distearate, polypropylene glycol ester or fatty acid, and polytetramethylene oxide glycol distearate, waxes, stearic acid and waxes, metal stearate and waxes, metal stearate and stearic acid. The use of stearic acid alone do not reduce tack. The amount of stearic acid is also important. As an example, ratio of 200 grams stearic acid to 2,000 gram of S-EB-S (a ratio of 0.1) will result in spotted tack reduction on the surface of the gel. A ratio of 250 to 2,000 will result in spotted crystallized stearic acid regions on the surface of the gel or spotted tack reduction. A ratio of 300 to 2,000 will result in complete tack reduction with large stearic acid crystallized regions on the surface of the gel. When microcrystalline waxes are incorporated together with stearic acid, the crystallization of stearic acid completely disappears from the surface of the gel. For example excellent result is achieved with 200 grams of stearic acid, 150 grams of microcrystalline wax and 2,000 grams of S-EB-S. The same excellent result is achieved when S-EB-S is adjusted to 3,000 grams, 4,000 grams, etc. The same result is achieved with (I) copolymers as well as in combination with polymers (II) such as SEPS, S-EB-EP-S, (S-EB-EP)n, (SEB)n, (SEP)n polymers.

The stearic acid and microcrystalline wax components of the gels described in my earlier U.S. Pat. No. 5,760,117 are non-sticky, non-tacky and non-adhering. The non-adhering gels containing additives such as stearic acid and the like, however, feels greasy due the additive's high solubility in oil and low melting points forming a greasy coating on the surface of the gel.

More advantageously I have discovered non-tacky crystal gels which are non-tacky requiring no additive. Its non-tackiness are an inherent property of the crystallinity and glassy A components of the gels. Such non-tacky gels, however, must have the following criteria:

(1) the non-tacky gels are made from A-Z-A, (A-Z)n, (A-Y)n and (Y-AY)n copolymers: crystalline block copolymers and crystalline poly(ethylene-styrene) random copolymers of the type S, M, and E series (for example SEEPS, S-E-EB-S, S-EB45-EP-S, S-E-EB25-S, S-E-EP-E-S, S-EP-E-S, S-EP-E-EP-S, E-S-E, (E-S)n, (E-S-E)n, and(S-E-EP)n, crystalline S-EB-S with ethylene to butylene midblock ratios (E:B) of 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, and 70:30) and the like;

(2) the non-tacky gels are made from copolymers having crystalline poly(ethylene) segments exhibit melting endotherm values of at least about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., and higher; and (3) the non-tacky gels are made from copolymers having glassy A to Y or glassy A to Z ratios of at least 37:63, higher ratios are also of advantage such as 38:62, 39:61, 40:60, 41:59, 42:58, 43:57, 44:65, 45:55, 46:54, 47:53, 48:52, 49:51, 50:50, 51:49, 52:48, 53:47, 54:46, 55:45, 56:44, 57:43, 58:42, 59:41, 60:40, 61:39, 62:38, 63:37, 64:36, 65:35, 66:34.

It is believed that the combination of crystallinity and high glassy A components of the copolymers imparts non-tackiness to the crystal gels of the invention. It is therefore contemplated that the same effect can be achieved by blending crystalline and high glassy copolymers with less crystalline and less glassy copolymers such as amorphous SEPS and amorphous S-EB-EP-S and other amorphous copolymers provided the amorphous copolymers are in minor amounts and there is substantial crystallinity and sufficient glassy A components so that conditions (2) and (3) are met.

The inherently non-tacky gels which is an improvement over the greasy feeling gels of U.S. Pat. No. 5,760,117 described above, although feels non-adhering and completely non-tacky and non-greasy, can exhibit a high coefficient of friction or high COF.

Figure 5:
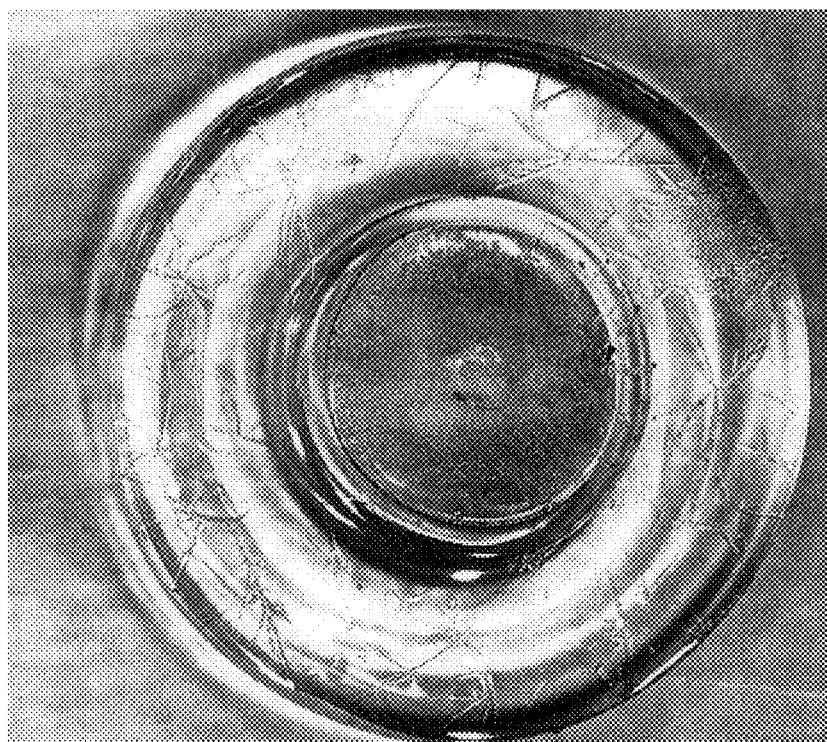
FIG. 5. Photocopy of the top of a crystal gel article made with phenolics only.

I have also found that by incorporating sufficient amounts of one or more of a selected (high melting, low oil soluble, and polar) low COF agents (such as polyphenolics with one or more sterically hindered phenolic hydroxyl groups) in the gels will result in the appearance of large crystals in the interior as well as on the surface of the gels. Such crystals are shown in FIG. 5 (top view) photo of the top of a crystal gel article with phenolic crystals. These crystals have no effect on the high COF of the resulting gels. Contrary to the combined effects of stearic acid and microcrystalline wax, the presence of microcrystalline wax with polyphenolic in gels does not lessen the gel's COF and have little effect on reducing the size of the large polyphenolic crystals. Likewise the crystallinity and glassy components by themselves can not by themselves reduce the inherent high COF of these gels. Consequently, gels containing microcrystalline wax and polyphenolics exhibit high COF.

Surprisingly, when selected amounts of internal nucleating agents are incorporated in the gels in combination with selected amounts of one or more of a low COF agents, the large crystals no longer forms within the gels; and the surface of the gels exhibit lower and lower COF with time. Bringing the gels in contact with selected external nucleating agents decreases the time or totally eliminates the time needed for the gel's outer surface to exhibit a low COF.

The gels and soft elastomers incorporating low COF agents and internal and/or external nucleating agents exhibit a much lower coefficient of friction when measured in contact with a reference surface than gels and soft elastomers made without such components.

School book physics teaches COF can be determined experimentally, for two given surfaces that are dry and not lubricated, the ratio of the tangential force needed to overcome the friction to the normal force which holds the two surfaces in contact (e.g., the weight of a block of gel or elastomer material on a surface) is a constant, independent of the area or of the velocity with which the surfaces (surface of a side of the block in contact with another surface) move over wide limits. This ratio is $\mu$, the coefficient of friction. The coefficient of sliding friction for a block of material being $$\mu = (f/F_n)$$

where f is the force of friction, and $F_n$ the normal force. For the case of the block on the horizontal table, if m is the mass of the block, then mg is the normal force and the above equation can be written as $$\mu = f/mg.$$

In the case the block of a block rests on a board, originally horizontal, and that the board then is tilted until a limiting angle $\phi$ is reached, beyond which the block will begin to slide down the board. At this angle the component of the weight of the object along the board is just equal in amount to that necessary to overcome the force of friction. The force down the plane is mg sin $\phi$, while the normal force is mg cos $\phi$. Therefore we have $$\mu = (mg \sin \phi)/(mg \cos \phi) \text{ or } \mu = \tan \phi.$$

The limiting value of $\phi$ for which $\mu = \tan \phi$ is true is call the angle of repose. Measurement of the tangent of this angle will give the coefficient of friction of the contacting surfaces of the block and the board that slide one upon the other.

As an example of low COF agents advantageously useful in soft thermoplastic elastomers and gels, excellent results is achieved with 50 grams of a polyphenolic with sterically hindered phenolic hydroxyl groups (Irganox 1010), about 100 grams of one or more nucleating agents (such as very fine particle size sodium benzoate, dibenzylidene sorbitol, its alkylated derivatives, talc, zinc steurates, amorphous silica, aluminum sterates, etc.) and 5,000 grams of S-EB-S and 25,000 gram of oil. The same excellent result is achieved when S-EB-S is adjusted to 3,000 grams, 4,000 grams, etc. The same result is achieved with copolymers as well as in combination with other polymers. Moreover, when about 50 grams of tetrakis[methylene 3,-(3'5'-ditertbutyl-4"-hydroxyphenyl) propionate] methane is use (per about 22.68 Kilograms or 50 lbs of gel) as a low COF agent, tack is completely removed from the surface of the gel after two to three weeks of blooming.

Figure 6:
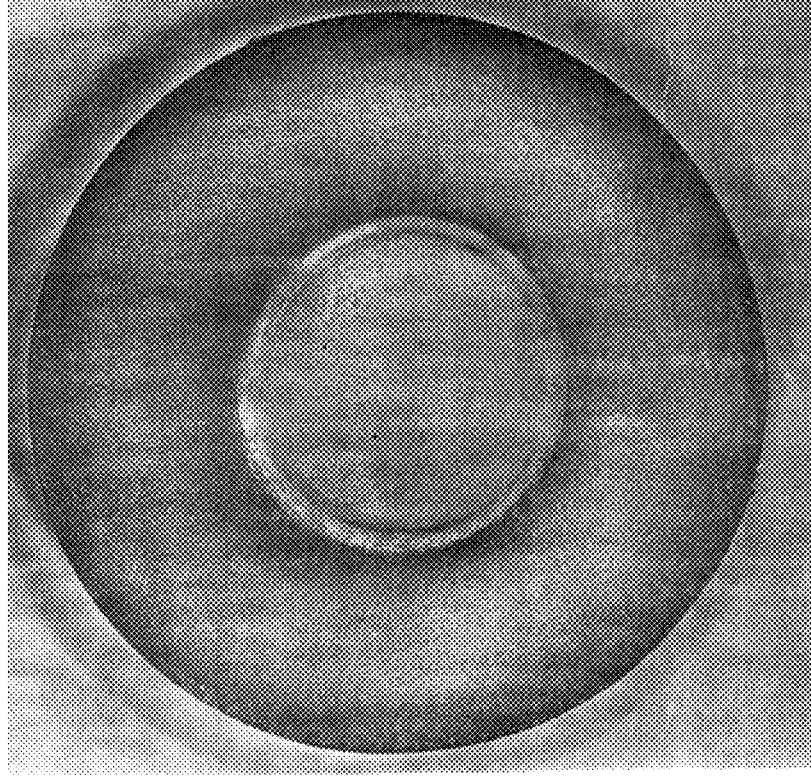
FIG. 6. Photocopy of the top of a crystal gel article made with phenolics and external nucleating agents.

When this is repeated with an external nucleating agent, such as with various fine particles for coating the outside surface of the elastomer or gel, such as with talc, calcium stearate, zinc sterate, amorphous silica, aluminum sterate, fine flour, corn starch, fine soil, fine sand, fine metallic powder, vacuum dust, fine wood dusts and the like, lower COF is achieved within a few days to less than several hours. After coating the gel for the desired period of time, the fine polar and water soluble particles can be washed off with water and soap, while non-polar and non-water soluble fine powders can be removed by wearing it off or by lifting it off with the use of adhesive tapes if so desired. FIG. 6. (top view) photo of the top of a crystal gel article made with phenolics and external nucleating agents.

What is the surface properties of low COF agents at the air/plasticizer-copolymer interface? Theory notwithstanding, the resulting gel surface will comprise of very fine molecular segments or even very fine crystal grains of low COF agents confined at the air/plasticizer and polymer interface. Depending on concentration, the non-polar segments of the low COF agents will have a tendency of being adsorpted by the predominate plasticizer and copolymer midblock phase at the gel surface. The slightly polar or more polar segments of the low COF agents are adsorbed to a lesser extent by the plasticizer-copolymer surface. This is supported by observing the water wetting characteristics at the gel surface with and with out low COF agents at the air gel surface interface. A drop of water will bead up and not readily wet the gel surface free of any low COF agents (hydrophobic). The presence of even slightly polar low COF agents exposed on the surface of the gel will make a drop of water flatten out and not bead up when place on the gel surface (hydrophilic).

Commercial high melting point, low oil solubility, and polar low COF agents such as polyphenolics which are advantageously useful in the present invention include: Ethanox 330 (Ethyl), Irganox 1010 (Ciba-Geigy), Santechhem A/O 15-1 (Santech), Ultra 210 (GE), Hostanox 03 (Hoechst Celanese), Irganox 3114 (Ciba-Geigy), Mixxim AO-3 (Fairmont), and the like.

Copolymer for forming the low COF compositions include block copolymers, random copolymers, metallocene catalyzed ethylene-styrene copolymers, Low COF crystal gels made from thermoplastic elastomer copolymers and block copolymers having one or more substantially crystalline polyethylene segments or midblocks. The low COF crystal gels advantageously exhibit high, higher, and higher, and ever higher tear resistance than realized before as well as improved high tensile strength. The low COF crystal gels also exhibit improved damage tolerance, crack propagation resistance and especially improved resistance to high stress rupture which combination of properties makes the gels advantageously and surprisingly suitable for use as toys, inflatable air cushions in automobiles, and the like.

The crystal gels of this invention are advantageously useful for making low COF gel compositions. Moreover, various polymer gels made from linear triblock copolymers, multi-arm block copolymers, branched block copolymers, radial block copolymers, multiblock copolymers, random/non-random copolymers, thermoplastic crystalline polyurethane copolymers with hydrocarbon midblocks or mixtures of two or more of such copolymers can also be made with low COF. The COF values of the crystal gels formed form the low COF and nucleating agents are found to be about less than 1, more advantageously less than 0.7, more advantageously less than 0.577, still more advantageously less than 0.466 and still more advantageously less tan 0.40. The low COF crystal gels of the invention can range from less than 1.0 to about less than 0.40.

The crystal gels can also contain useful amounts of conventionally employed additives such as stabilizers, antioxidants, antiblocking agents, colorants, fragrances, flame retardants, flavors, other polymers in minor amounts and the like to an extend not affecting or substantially decreasing the desired properties. Additives useful in the crystal gel of the present invention include: tetrakis [methylene 3,-(3',5'-di-tertbutyl-4"-hydroxyphenyl) propionate] methane, octadecyl 3-(3",5"-di-tert-butyl-4"-hydroxyphenyl) propionate, distearyl-pentaerythritol-diproprionate, thiodiethylene bis-(3,5-ter-butyl-4-hydroxy) hydrocinnamate, (1,3,5-trimethyl-2,4,6-tris[3,5-di-tert-butyl-4-hydroxybenzyl] benzene), 4,4"-methylenebis(2,6-di-tert-butylphenol), stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, calcium sterate, other metal sterates, waxes (e.g., polyethylene, polypropylene, microcrystalline, carnauba, paraffin, montan, candelilla, beeswax, ozokerite, ceresine, and the like), teflon (TFE, PTFE, PEA, FEP, etc), polysiloxane, etc. The crystal gel can also contain metallic pigments (aluminum and brass flakes), $TiO_2$, mica, fluorescent dyes and pigments, phosphorescent pigments, aluminatrihydrate, antimony oxide, iron oxides ($Fe_3O_4$, —$Fe_2O_3$, etc.), iron cobalt oxides, chromium dioxide, iron, barium ferrite, strontium ferrite and other magnetic particle materials, molybdenum, silicones, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on Magnetic Materials, Publication NMAB-426, National Academy Press (1985) is incorporated herein by reference.

The crystal gels can also be made into composites. The crystal gels can be casted unto various substrates, such as open cell materials, metals, ceramics, glasses, and plastics, elastomers, fluropolymers, expanded fluropolymers, Teflon (TFE, PTFE, PEA, FEP, etc), expanded Teflon, spongy expanded nylon, etc.; the molten crystal gel is deformed as it is being cooled. Useful open-cell plastics include: polyamides, polyimides, polyesters, polyisocyanurates, polyisocyanates, polyurethanes, poly(vinyl alcohol), etc. Suitable open-celled Plastic (sponges) are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

The crystal gels denoted as "G" can be physically interlocked with a selected material denoted as "M" to form composites as denoted for simplicity by their combinations GnGn, GnGnGn, GnMn, GnMnGn, MnGnMn, MnGnGn, GnGnMn, MnMnMnGn, MnMnMnGnMn, MnGnGnMn, GnMnGnGn, GnMnMnGn, GnMnMnGn, GnGnMn Mn, GnGnMn GnMn, GnMnGnGn, GnGnMn, GnMnGnMnMn, MnGnMnGnMnGn, GnGnMnMnGn, GnGnMnGnMnGn, and the like or any of their permutations of one or more Gn with Mn and the like, wherein when n is a subscript of M, n is the same or different selected from the group consisting of paper, foam, plastic, fabric, metal, concrete, wood, glass, ceramics, synthetic resin, synthetic fibers or refractory materials and the like; wherein when n is a subscript of G, n denotes the same or a different gel rigidity of from about 2 gram to about 1,800 gram Bloom). The crystal gels of the composites are formed from copolymers (I), polymers (II), and plasticizers (III) described above.

Sandwiches of crystal gel-material (i.e., crystal gel-material- crystal gel or material-crystal gel-material, etc.) are useful as dental floss, shock absorbers, acoustical isolators, vibration dampers, vibration isolators, and wrappers. For example the vibration isolators can be use under research microscopes, office equipment, tables, and the like to remove background vibrations. The tear resistance nature of the instant crystal gels are superior in performance to amorphous block copolymer gels which are much less resistance to crack propagation caused by long term continue dynamic loadings.

The crystal gels are prepared by blending together the components including other additatives as desired at about 230° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amounts of multiblock copolymers (I) and polymer (II) used. These components blend easily in the melt and a heated vessel equipped with a stirrer is all that is required. Small batches can be easily blended in a test tube using a glass stirring rod for mixing. While conventional large vessels with pressure and/or vacuum means can be utilized in forming large batches of the instant crystal gels in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than 10 rpm to about 40 rpm or higher.

The crystal gel articles can be formed by blending, injection molding, extruding, spinning, casting, dipping and other conventional methods. For example, Shapes having various cross-section can be extruded. The crystal gels can also be formed directly into articles or remelted in any suitable hot melt applicator and extruded into shaped articles and films or spun into threads, strips, bands, yarns, or other shapes. With respect to various shapes and yarn, its size are conventionally measured in denier (grams/9000 meter), tex (grams/1000 meter), and gage (1/2.54 cm). Gage, tex, denier can be converted as follows: tex=denier/9=specific gravity (2135/gage), for rectangular cross section, tex=specific gravity (5806×103)(th)(w)/9, where th is the thickness and w the width of the strip, both in centimeters. General descriptions of (1) block copolymers, (2) elastomeric fibers and conventional (3) gels are found in volume 2, starting at pp. 324–415, volume 6, pp 733–755, and volume 7, pp. 515 of ENCYCLOPEDIA OF POLYMER SCIENCE AND ENGINEERING, 1987 which volumes are incorporated herein by reference.

The crystal gels are excellent for cast molding and the molded products have various excellent characteristics which cannot be anticipated form the properties of the raw components. Other conventional methods of forming the composition can be utilized.

Not only do the crystal gels have all the desirable combination of physical and mechanical properties substantially similar to high viscosity amorphous S-EB-S gels such as high elongation at break of at least 1,600%, ultimate tensile strength of about 8×105 dyne/cm2 and higher, low elongation set at break of substantially not greater than about 2%, substantially about 100% snap back when extended to 1,200% elongation, and a gel rigidity of substantially from about 2 gram to about 1,800 gram Bloom and higher, the crystal gels of the present invention exhibit improved tear resistance and resistance to fatigue not obtainable from amorphous S-EB-S gels at corresponding gel rigidities.

The crystal gels of the present invention exhibit one or more of the following properties. These are: (1) tensile strength of about 8×105 dyne/cm2 to about 107 dyne/cm2 and greater; (2) elongation of less than about 1,600% to about 3,000% and higher; (3) elasticity modules of about 104 dyne/cm2 to about 106 dyne/cm2 and greater; (4) shear modules of about 104 dyne/cm2 to about 106 dyne/cm2 and greater as measured with a 1, 2, and 3 kilogram load at 23° C.; (5) gel rigidity of about less than about 2 gram Bloom to about 1,800 gram Bloom and higher as measured by the gram weight required to depress a gel a distance of 4 mm with a piston having a cross-sectional area of 1 square cm at 23° C.; (6) tear propagation resistance greater than the tear resistance of amorphous S-EB-S gels at corresponding gel rigidities; (7) resistance to fatigue greater than the fatigue resistance of amorphous S-EB-S gels at corresponding gel rigidities; (8) and substantially 100% snap back recovery when extended at a cross-head separation speed of 25 cm/minute to 1,200% at 23° C. Properties (1), (2), (3), and (6) above are measured at a crosshead separation speed of 25 cm/minute at 23° C.

The crystal gel articles molded from the instant crystal gels have additional important advantages in that they end-use performance properties are greater than amorphous S-EB-S gels in that they are more resistant to cracking, tearing, crazing or rupture in flexural, tension, compression, or other deforming conditions of use. Like amorphous gels, the molded articles made from the instant composition possess the intrinsic properties of elastic memory enabling the articles to recover and retain its original molded shape after many extreme deformation cycles.

Because of their improved tear resistance and improved resistance to fatigue, the crystal gels of the present invention achieve greater performance than amorphous gels in low frequency vibration applications, such as viscoelastic layers in constrained-layer damping of mechanical structures and goods, as viscoelastic layers used in laminates for isolation of acoustical and mechanical noise, as anti-vibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components.

Because of their improved tear resistance and improved resistance to fatigue, the crystal gels are more useful as molded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes. Other uses include various shaped articles as toys, optical uses (e.g., cladding for cushioning optical fibers from bending stresses) and various optical devices, as lint removers, dental floss, as tips for swabs, as fishing bate, as a high vacuum seal (against atmosphere pressure) which contains a useful amount of a mineral oil-based magnetic fluid particles, etc. Moreover, the casted, extruded, or spun threads, strips, yarns, tapes can be weaved into cloths, fine or coarse fabrics. The weaved crystal gels are of great advantage for forming orthotics and prosthetic articles described above because such devices made from weaved crystal gels of fine to corsed fabrics will allow for the human skin to breathe. The openings between weaved strands allows for air and oxygen transport between the skin and outer portions of the gel device body. Moreover, fine oriented or non-oriented crystal gels (made from SEEBS, SEEPS, E-S-E, SEEPES, SEPEEPS, $SEB_{45}S$ and the like) in the form of threads or yarns can be produced by extruding, spinning or forced through a collection of jet nozzles to form a crystal gel spray to produce porous gel non-woven matting or webs which are skin oxygen/air breathe-able fabrics and articles. Unlike the elastomeric nonwoven webs made at 290° C. of U.S. Pat. No. 4,692,371, the crystal gels must be formed advantageously below 180° C., more advantageously at about 175° C. or lower because of the extremely high amount of plasticizer components. If the crystal gels are heated to above 200° C. and higher, the result is a puddle of hot liquid gel mass and not the porous individual form strands forming the desired fabrics. Furthermore, the crystal gels are superior in properties than any gels made from amorphous SEBS gels of substantially corresponding rigidities.

Porous, webbing or matting that are skin breathe-able comprising crystal gel strands can be formed into a webs or matting by cold forming sandwiched crystal gels strand-composites using alkyl cyanoacrylates such as ethyl, butyl, methyl, propyl cyanoacrylates and the like. The alkyl cyanoacrylates (AC) will interlock with the gels of the invention, thereby resulting in gel-(AC)-gel composite webbing or matting articles. Alkyl cyanoacrylates are useful for interlocking crystal gels of the invention with other substrates such as pottery, porcelain, wood, metal, plastics, such as acrylics, ABS, EPDM, nylon Fiberglass, phenoics, plexiglass, polycarbonate, polyesters, polystyrene, PVC, urethanes and the like. Other cyanoacrylates such as cyanoacrylate ester are inhibited interlocking with the crystal gels of the invention.

The crystal gels can be formed in any shape; the original shape can be deformed into another shape (to contact a regular or irregular surface) by pressure and upon removal of the applied pressure, the composition in the deformed shape will recover back to its original shape.

As an example of the versatility of use of the instant crystal gels, a hand exerciser can be made in any shape so long as it is suitable for use as a hand exerciser: a sphere shape, a cube shape, a rectangular shape, etc. Likewise, a wheelchair cushion can be made from the composition in any shape, so long as it meets the needs of the user of the cushion. For example, a cushion can be made by forming the composition into a selected shape matching the contours of the specific body part or body region. The composition can be formed into any desired shaped, size and thickness suitable as a cushion; the shaped composition can be additionally surrounded with film, fabric, foam, or any other desired material or combinations thereof. Moreover, the composition can be casted onto such materials, provided such materials substantially maintain their integrity (shape, appearance, texture, etc.) during the casting process. The same applies for brace cushions, liners, linings and protective coverings for the hand, wrist, finger, forearm, knee, leg, etc.

Because of their improved tear resistance and resistance to fatigue, the crystal gels exhibit versatility as balloons for medical uses, such as balloon for valvuloplasty of the mitral valve, gastrointestinal balloon dilator, esophageal balloon dilator, dilating balloon catheter use in coronary angiogram and the like. Since the crystal gels are more tear resistant, they are especially useful for making condoms, toy balloons, and surgical and examination gloves. As toy balloons, the crystal gels are safer because it will not rupture or explode when punctured as would latex balloons which often times cause injures or death to children by choking from pieces of latex rubber. The crystal gels are advantageously useful for making gloves, thin gloves for surgery and examination and thicker gloves for vibration damping which prevents damage to blood capillaries in the fingers and hand caused by handling strong shock and vibrating equipment.

Other uses include self sealing enclosures for splicing electrical and telephone cables and wires. For example, the crystal gels can be pre-formed into a small diameter tubing within an outer elastic tubing, both the internal crystal gel tubing and external elastic tubing can be axially expanded and fixed in place by a removable continuous retainer. Upon insertion of a spliced pair or bundle of cables or wires, the retainer can be removed, as the retainer is removed, the crystal gel and elastic tubing impinges onto the inserted cables or wires splices, thereby sealing the electrical splices against weather, water, dirt, corrosives and shielding the splice from external abuse. The enclosure is completed without the use of heat or flame as is conventionally performed.

Because of their improved resistance to tearing, the crystal gels do not tear as readily as amorphous gels when used as dental floss. The dental floss can be almost any shape so long as it is suitable for dental flossing. A thick shaped piece of the composition can be stretched into a thin shape and used for flossing. A thinner shaped piece would require less stretching, etc. For purposes of dental flossing, while flossing between two closely adjacent teeth, especially between two adjacent teeth with substantial contact points and more especially between two adjacent teeth with substantial amalgam alloy metal contact points showing no gap between the teeth, it is critical that the crystal gel resist tearing, shearing, and crazing while being stretched to a high degree in such situations. For example, dental crystal gel floss can take the form of a disk where the segments of the circumference of the disk is stretched for flossing between the teeth. Other shaped articles suitable for flossing include threads, strips, yarns, tapes, etc., mentioned above.

In order for crystal gels to be useful as a dental floss, it must overcome the difficult barriers of high shearing and high tearing under extreme elongation and tension loads. The difficulties that the crystal gels must overcome during flossing can be viewed as follows: during the action of flossing, the crystal gel is stretched from no less than about 200% to about 1,100% or higher, the crystal gel floss is deformed as it is pulled down with tearing action between the contacting surfaces of the teeth, then, the wedge of crystal gel floss is sheared between the inner contacting surfaces of the teeth, and finally, the elongated wedged of crystal gel floss is pulled upwards and out between the surfaces of the teeth. The forces encountered in the act of flossing are: tension, shearing, tearing under extreme tension.

The use of crystal gels advances the flossing art by providing strong, soft, and more tear resistant gels than amorphous gels. Floss made from the crystal gels has many advantages over conventional dental floss such as regular and extra fine waxed and unwaxed nylon floss, spongy nylon fiber floss, and waxed and unwaxed expanded and unexpended teflon floss. Such conventional floss are not recommended for use by children, since a slip or sudden snap in forcing the floss between the teeth may cause injury to the gums which often times results in bleeding. For sensitive gums and inflamed gums which has become red and puffy, it is difficult to floss at, near, and below the gumline. The soft crystal gel floss with softness substantially matching the softness of the gums are of great advantage for use by children and for flossing teeth surrounded by sensitive and tender gums.

In all cases, the tear strength of crystal gels are higher than that of amorphous gels. The rigidities of the crystal gels for use as dental floss advantageously should be selected to exhibit a propagating tear force (when propagating a tear as measured at 180o U bend around a 5.0 mm diameter mandrel attached to a spring scale) of at least about 1 Kg/cm, more advantageously at least 2 Kg/cm, and still more advantageously of about 3 Kg/cm and higher. For any gel to be considered useful for flossing, the gels should exhibit tear strengths of at least 2 Kg/cm and higher, advantageously of at least 4 Kg/cm and higher, more advantageously of at least 6 Kg/cm and higher, exceptionally more advantageously of at least 8 Kg/cm and higher. Typically, the tear propagation strength should range from about 5 Kg/cm to about 20 Kg/cm and higher, more typically from about less than 5 Kg/cm to about 25 Kg/cm and higher, especially more typically form about less than 6 Kg/cm to about 30 Kg/cm and higher, and exceptionally more typically from about less than 8 Kg/cm to about 35 Kg/cm and higher.

For any gel to be considered useful for flossing, the gels, critically, should advantageously exhibit a propagating tension tear force (when a cylindrical sample is notched and a tear is initiated at the notched area and propagated past its maximum cylindrical diameter by length-wise stretching of the cylindrical sample) of at least about 1 Kg/cm, more advantageously at least 2 Kg/cm, and still more advantageously of about 4 Kg/cm and higher. Although the crystal gels of the present invention have improved tear resistance and resistance to fatigue greater than the amorphous gels at corresponding gel rigidities, the high and ultra-high tear resistant gels of my other related parent and c-i-p applications typically will exhibit even higher tear resistance values.

The crystal gels of the invention can be use for making air bags. The expansion of the gel air bag is substantially pure volume expansion or dilation as related to K, bulk modulus, y, young's modulus: K=y/3(1-2t), t=3k-2n/6k-2n, where t=poisson's ratio, b=1/k compressibility=-change in V/(V·change in pressure P).

Surface expansion measure of air bag from initial to expanded state is from 630 to 833% depending on thickness of original air bag. The initial air bag thickness can vary from 0.5 cm to 10 cms. (0.5, 1, 2, 3, 4, 5, 6, 7, 8, 9, 10 cm and higher).

While advantageous components and formulation ranges based on the desired properties of the crystal gels have been disclosed herein. Persons of skill in the art can extend these ranges using appropriate material according to the principles discussed herein. All such variations and deviations which rely on the teachings through which the present invention has advanced the art are considered to be within the spirit and scope of the present invention.

The invention is further illustrated by means of the following illustrative embodiments, which are given for purpose of illustration only and are not meant to limit the invention to the particular components and amounts disclosed.

EXAMPLE I

Gels of 100 parts of high viscosity linear Kraton G1651 (amorphous S-EB-S), Septon 8006 (amorphous S-EB-S), Septon S2006 (amorphous S-EP-S) and a high viscosity radial amorphous midblock segment (SEB)n triblock copolymers and 1,600, 1,200, 1,000, 800, 600, 500, 450, 300, 250 parts by weight of Duraprime 200 white oil (plasticizer) are melt blended and samples molded, the bulk gel rigidities are found to be within the range of 2 to 1,800 gram Bloom and the tensile strength, notched tear strength, and resistance to fatigue are found to decrease with increase amounts of plasticizers.

EXAMPLE II

Example I is repeated using high viscosity crystalline midblock segment linear S-EB-S and radial (SEB)n triblock copolymers with ethylene to butylene midblock ratios (E:B) of 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, and 70:30 in combination with an equal amount of amorphous S-EB-S having (E:B) ratio of about 60:40, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE III

Gels of 100 parts of Kraton G1651 (amorphous S-EB-S), Septon 8006 (amorphous S-EB-S), and a high viscosity amorphous midblock segment (SEB)n linear and radial triblock copolymers, 1,600, 1,200, 1,000, 800, 600, 500, 450, 300, 250 parts by weight of Duraprime 200 white oil (plasticizer), and 10 parts of Dow polydimethylsiloxane are melt blended and samples molded, the bulk gel rigidities are found to be within the range of 2 to 1,800 gram Bloom and the tensile strength, notched tear strength, and resistance to fatigue are found to decrease with increase amounts of plasticizers.

EXAMPLE IV

Gels of 100 parts of Kraton G1651 (amorphous S-EB-S), Septon 8006 (amorphous S-EB-S), and a high viscosity amorphous midblock segment (SEB)n linear and radial triblock copolymers, 1,600, 1,200, 1,000, 800, 600, 500, 450, 300, 250 parts by weight of Duraprime 200 white oil (plasticizer), and 2 parts of Dupont Teflon AF 1600 are melt blended and samples molded, the bulk gel rigidities are found to be within the range of 2 to 1,800 gram Bloom and the tensile strength, notched tear strength, and resistance to fatigue are found to decrease with increase amounts of plasticizers.

EXAMPLE V

Example III is repeated using high viscosity crystalline midblock segment linear S-EB-S and radial (SEB)n triblock copolymers with ethylene to butylene midblock ratios (E:B) of 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, and 70:30 in combination with an equal amount of amorphous S-EB-S having (E:B) ratio of about 60:40, the bulk gel rigidities are found to be within the range of 2 gram to 1,800 gram Bloom and the notched tear strength and resistance to fatigue of the gel at corresponding rigidities are found to be greater than that of amorphous gels of Example III.

EXAMPLE VI

Example IV is repeated using high viscosity crystalline midblock segment linear S-EB-S and radial (SEB)n triblock copolymers with ethylene to butylene midblock ratios (E:B) of 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, and 70:30 in combination with an equal amount of amorphous S-EB-S having (E:B) ratio of about 60:40, the bulk gel rigidities are found to be within the range of 2 gram to 1,800 gram Bloom and the notched tear strength and resistance to fatigue of the gel at corresponding rigidities are found to be greater than that of amorphous gels of Example IV.

EXAMPLE VII

Gels of 100 parts of high viscosity (S-EB-S), (S-EP-S), (S-EB-EP-S), (S-EB)n, (S-EP)n (S-EB-EP)n block copolymers and 1,600, 1,200, 1,000, 800, 600, 500, 450, 300, 250 parts by weight of Duraprime 200 white oil (plasticizer) are each melt blended and samples molded, the bulk gel rigidities are found to be within the range of 2 to 1,800 gram Bloom and the tensile strength, notched tear strength, and resistance to fatigue are found to decrease with increase amounts of plasticizers.

EXAMPLE VIII

Gels of 100 parts of high viscosity linear (S-EB$_{45}$-EP-S), (S-E-EB$_{25}$-S), (S-EP-E-EP-S), (S-E-EB-S), (S-E-EP-S), (S-E-EP-E-S), (S-E-EP-EB-S), (S-E-EP-E-EP-S), (S-E-EP-E-EB-S), (S-E-EP-E-EP-E-S), (S-E-EP-E-EB-S), (S-E-EP-E-EP-EB-S), and (S-E-EP-E-EP-E-S) block copolymers and 1,600, 1,200, 1,000, 800, 600, 500, 450, 300, 250 parts by weight of Duraprime 200 white oil (plasticizer) are each melt blended and samples molded, the bulk gel rigidities are found to be within the range of 2 to 1,800 gram Bloom and the tensile strength, notched tear strength, and resistance to fatigue are found to be greater than that of amorphous gels of Example VII.

EXAMPLE IX

Example VIII is repeated and minor amounts of 2, 5, 10 and 15 parts of the following polymers are formulated with each of the triblock copolymers: styrene-butadiene-styrene block copolymers, styrene-isoprene-styrene block copolymers, low viscosity styrene-ethylene-butylene-styrene block copolymers, styrene-ethylene-propylene block copolymers, styrene-ethylene-propylene-styrene block copolymers, styrene-butadiene, styrene-isoprene, polyethyleneoxide, poly(dimethylphenylene oxide), polystyrene, polybutylene, polyethylene, polypropylene, high ethylene content EPDM, amorphous copolymers based on 2,2-bistrifluoromethyl-4,5-difuoro-1,3-dioxole/ tetrafluoroethylene. The bulk gel rigidities of each of the formulations are found to be within the range of 2 gram to 2,000 gram Bloom and the notched tear strength and resistance to fatigue of the gels at corresponding rigidities are found to be greater than that of amorphous gels of Example I formulated with corresponding amounts of the same polymers.

EXAMPLE X

Molten gels of Examples I–bIX are formed into composites with paper, foam, plastic, elastomers, fabric, metal, concrete, wood, glass, ceramics, synthetic resin, synthetic fibers, and refractory materials and the resistance to fatigue of the composite-crystal gels at corresponding rigidities are found to be greater than that of the composite-amorphous gels.

EXAMPLE XI

Three cm thick sheets of each of the crystal gels of Example II and VIII and the amorphous gels of Example I and VII are tested by repeatedly displacing the sheets to a depth of 1 cm using a 10 cm diameter smooth (water soaked) wood plunger for 1,000, 5,000, 10,000, 25,000, 50,000, and 100,000 cycles. The sheets of crystal gels are found capable of exhibiting greater fatigue resistance than the sheets of amorphous gels at corresponding rigidities.

EXAMPLE XII

Gels of 50 parts of Dow S series (Mw=340,000/Melt Index=0.18/Tg 30° C.), M series (Mw=240,000/Melt Index= 0.08/Tg 20° C.) and E series (Mw=240,000/Melt Index 0.03/Tg –8° C.) poly(ethylene-styrene) random copolymers in combination with 50 parts of Kraton G1651 (amorphous S-EB-S) and 1,600, 1,200, 1,000, 800, 600, 500, 450, 300, 250 parts by weight of Duraprime 200 white oil (plasticizer) are each melt blended and samples molded, the bulk gel rigidities are found to be within the range of 2 to 1,800 gram Bloom and the tensile strength, notched tear strength, and resistance to fatigue are found to be greater than that of amorphous gels of Example VII.

EXAMPLE XIII

Gels of 50 parts of Dow S series (Mw=340,000/Melt Index=0.18/Tg 30° C.), M series (Mw=340,000/Melt Index= 0.05/Tg 10° C.) and E series (Mw=340,000/Melt Index 0.01/Tg –15° C.) poly(ethylene-styrene) random copolymers in combination with 50 parts of Septon S2006 (amorphous S-EP-S) and 1,600, 1,200, 1,000, 800, 600, 500, 450, 300, 250 parts by weight of Duraprime 200 white oil (plasticizer) are each melt blended and samples molded, the bulk gel rigidities are found to be within the range of 2 to 1,800 gram Bloom and the tensile strength, notched tear strength, and resistance to fatigue are found to be greater than that of amorphous gels of Example VII.

EXAMPLE XIV

Gels of 100 parts of Septon 4045, 4033, 4055 and 4077 and 1,600, 1,200, 1,000, 800, 600, 500, 450, 300, 250 parts by weight of Duraprime 200 white oil (plasticizer) are each melt blended and samples molded, the bulk gel rigidities are found to be within the range of 2 to 1,800 gram Bloom and the tensile strength, notched tear strength, and resistance to fatigue are found to be greater than that of amorphous gels of Example VII.

EXAMPLE XIV

Gels of 50 parts of Septon 4045, 4033, 4055 and 4077 in combination with 50 parts of Kraton G1651 (amorphous S-EB-S) and 1,600, 1,200, 1,000, 800, 600, 500, 450, 300, 250 parts by weight of Duraprime 200 white oil (plasticizer) are each melt blended and samples molded, the bulk gel rigidities are found to be within the range of 2 to 1,800 gram Bloom and the tensile strength, notched tear strength, and resistance to fatigue are found to be greater than that of amorphous gels of Example VII.

EXAMPLE XIV

Gels of 50 parts of Septon 4045, 4033, 4055 and 4077 in combination with 50 parts of Septon S2006 (amorphous S-EP-S) and 1,600, 1,200, 1,000, 800, 600, 500, 450, 300, 250 parts by weight of Duraprime 200 white oil (plasticizer) are each melt blended and samples molded, the bulk gel rigidities are found to be within the range of 2 to 1,800 gram Bloom and the tensile strength, notched tear strength, and resistance to fatigue are found to be greater than that of amorphous gels of Example VII.

EXAMPLE XV

Gels of 100 parts of Kraton G1651, Kuraray Septon 2006 (SEPS), Kuraray Septon 0 (SEBS), a high viscosity $(SEB)_n$, and a high viscosity $(SEP)_n$ triblock copolymers and 1,600, 1,200, 1,000, 800, 600, 500, 450, and 300 parts by weight of Duraprime 200 white oil are melt blended and samples extruded (from a 7.15 mm diameter orifice) into selected lengths of varying diameters for use as dental floss, the bulk gel rigidities is found to be within the range of 2 to 1,800 gram Bloom, the tensile strength is found to decrease with increase orientation.. and the optimum tensile strength found for gel samples with the least amount of stress or orientation imparted during cool from the molten state to room temperature.

EXAMPLE XVI

Example XV is repeated using Kuraray (S-E-EP-S) 4055 and 4077 multiblock copolymers, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE XV. The tensile strength is found to decrease with increase orientation, and the optimum tensile strength found for gel samples with the least amount of stress or orientation imparted during cool from the molten state to room temperature.

EXAMPLE XVII

Example XV is repeated using (S-E-EP-S), (S-E-EP-B-S), (S-B-EP-S), (S-E-EB-S), (S-EB-EP-S), (S-E-EP-EB-S), (S-B-EB-S), (S-E-EB-E-S), (S-B-EP-E-S), (S-B-EB-E-S), (S-B-EP-B-S), (S-B-EB-B-S), (S-E-E-EP-S), (S-E-E-EB-S), (S-B-E-EP-S), (S-B-E-EB-S), (S-B-B-EP-S), (S-B-B-EB-S), (S-E-B-EB-S), (S-E-B-EP-S), (S-EB-EB-S), (S-EP-EP-S), (S-E-EB-EB-S), (S-E-EP-EP-S), (S-E-EB-EP-S), (S-B-EB-EB-S), (S-B-EP-EP-S), (S-B-EB-EP-S), (S-B-EP-EB-S), (S-E-EP-E-EP-S), (S-E-EB-E-EB-S), (S-E-EP-E-EB-S), (S-B-EP-B-EP-S) (S-B-EB-B-EB-S), (S-B-EB-B-EP-S), (S-B-EB-E-BP-S), (S-B-EP-E-EP-S), (S-E-EB-B-EP-S), (S-E-EP-B-EB-S), (S-P-EB-S), (S-P-EP-S), (S-P-EP-P-S). (S-P-EB-P-S), (S-B-EP-P-S), (S-B-EB-P-S), (S-P-E-EP-S), (S-P-E-EB-S), (S-B-P-EP-S), (S-B-P-EB-S), (S-P-B-EB-S), (S-P-B-EP-S), (S-P-EB-EB-S), (S-P-EP-EP-S), (S-P-EB-EP-S), (S-P-EP-EB-S), (S-P-EP-P-EP-S), (S-P-EB-P-EB-S), (S-P-EP-P-EB-S), (S-B-EB-P-EB-S), (S-B-EP-P-EP-S), (S-P-EB-B-EP-S), (S-P-EP-B-EB-S), (S-E-EP-P-S), (S-E-EB-P-S), (S-E-P-EP-S), (S-E-P-EB-S), (S-E-EP-P-EP-S), (S-E-EB-P-EB-S), (S-E-EP-P-EB-S), (S-E-EP-E-EP-E-S), (S-B-EP-B-EP-B-S), (S-P-EP-P-EP-P-S), (S-E-EB-E-EB-E-S), (S-P-EP-P-EP-P-S), (S-E-EP)$_n$, (S-E-EP-E)$_n$, (S-B-EP)$_n$, (S-E-EB-S)$_n$, (S-EB-EP-)$_n$, (S-E-EP-EB)$_n$, (S-B-EB)$_n$, (S-B-EB-E)$_n$, (S-B-EP-E)$_n$, (S-B-EB-E)$_n$, (S-B-EP-B)$_n$, (S-B-EB-B)$_n$, (S-E-E-EP)$_n$, (S-E-E-EB)$_n$, (S-B-E-EP)$_n$, (S-B-E-EB)$_n$, (S-B-E-EP)$_n$, (S-B-B-EP)$_n$, (S-B-B-EP)$_n$, (S-E-B-EB)$_n$, (S-E-B-EP)$_n$, (S-EB-EB)$_n$, (S-EP-EP)$_n$, (S-E-EB-EB)$_n$, (S-E-EP-EP)$_n$, (S-E-EB-EP)$_n$, (S-B-EB-EB)$_n$, (S-B-EP-EP)$_n$, (S-B-EB-EP)$_n$, (S-B-EP-EB)$_n$, (S-E-EP-E-EP)$_n$, (S-E-EB-E-EB)$_n$, (S-E-EP-E-EB)$_n$, (S-B-EP-B-EP)$_n$, (S-B-EB-B-EB)$_n$, (S-B-EB-B-EP)$_n$, (S-B-EB-E-EB)$_n$, (S-B-EP-E-EP)$_n$, (S-E-EB-B-EP)$_n$, (S-E-EP-B-EB)$_n$, (S-P-EB)$_n$, (S-P-EP)$_n$, (S-P-EP-P)$_n$, (S-P-EB-P)$_n$, (S-B-EP-P)$_n$, (S-B-EB-P)$_n$, (S-P-E-EP)$_n$, (S-P-E-EB)$_n$, (S-B-P-EP)$_n$, (S-B-P-EB)$_n$, (S-P-R-EB)$_n$, (S-P-B-EP)$_n$, (S-P-EB-EB)$_n$, (S-P-EP-EP)$_n$, (S-P-EB-EP)$_n$, (S-P-EP-EB)$_n$, (S-P-EP-P-EP)$_n$, (S-P-EB-P-EB)$_n$, (S-P-EP-P-EB)$_n$, (S-B-EB-P-EB)$_n$, (S-B-EP-P-EP)$_n$, (S-P-EB-B-EP)$_n$, (S-P-EP-B-EB)$_n$, (S-E-EP-P)$_n$, (S-E-EB-P)$_n$, (S-E-P-EP)$_n$, (S-E-P-EB)$_n$, (S-E-EP-P-EP)$_n$, (S-E-EB-P-EB)$_n$, (S-E-EP-P-EB)$_n$, (S-E-EP-E-EP-E)$_n$, (S-B-EP-B-EP-B)$_n$, (S-P-EP-P-EP-P)$_n$, (S-E-EB-E-EB-E)$_n$, and (S-P-EP-P-EP-P)$_n$ multiblock copolymers, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE XV. The tensile strength is found to decrease with increase orientation, and the optimum tensile strength found for gel samples with the least amount of stress or orientation imparted during cool from the molten state to room temperature.

EXAMPLE XVIII

Example XVI is repeated using plasticizers L-14, L-50, L-100, H-15, H-25, H-35, H-50, H-100, H-300, L-14E, H-300E, Actipol E6, E16, E23, Kraton L-1203, EKP-206, EKP-207, HPVM-2203. Amoco C-60, Piccolyte S10, Duraprime (55, 70, 90, 200, 350, 400), Tufflo (6006, 6016, 6016M, 6026, 6036, 6056, 6206,) Bayol, Bernol, American, Blandol, Drakeol, Ervol, Gloria, and Kaydol, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE XV.

EXAMPLE XIX

Example XVII is repeated using plasticizers L-14, L-50, L-100, H-15, H-25, H-35, H-50, H-100, H-300, L-14E, H-300E, Actipol E6, E16, E23, Kraton L1203, EKP-206, EKP-207, HPVM-2203, Amoco C-60, Piccolyte S10, Duraprime (55, 70, 90, 200, 350, 400), Tufflo (6006, 6016, 6016M, 6026, 6036,6056, 6206,) Bayol, Bernol, American, Blandol, Drakeol, Ervol, Gloria, and Kaydol, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE XV.

EXAMPLE XX

A gel composition of 100 parts of Kuraray S-E-EP-S 4055 copolymer and 400 parts by weight of Duraprime 200 white oil was made following Example XV and extruded and drawn (from a 7.15 mm diameter orifice) into a strand of uniform diameter onto a take-up roll of continuous lengths. The strand diameter was varied by increasing and decreasing the speed of the take-up roll. The continuous strand of varying diameter gel strand was cut to suitable lengths for use and testing as dental floss. Additional gel was also casted in varying thickness and tested. The results of samples tested are shown in Table 3, #47; Table 4, #12–15 and 20; Table 5#22, 23, 27–29; Table 6#36–32; Table 7 #40–43, #76 and 77. Sample Nos. 76 and 77 were tested together. Sample 77 exhibited higher tensile strength after 27.75% of plasticizing oil was extracted (with 2.89 parts by weight of oil remaining), its rigidity remained substantially unchanged.

EXAMPLE XI

A gel composition of 100 parts of Kraton G1651 and 400 parts by weight of Duraprime 200 white oil was made following Example XV and extruded and drawn (from a 7.15 mm diameter orifice) into a strand of uniform diameter onto a take-up roll of continuous lengths. The strand diameter was varied by increasing and decreasing the speed of the take-up roll, The continuous strand of varying diameter gel strand was cut to suitable lengths for rise and testing as dental floss. Additional gel was also casted in varying thickness and tested. The results of samples tested are shown in Table 3B, #8–11,Table 4, #16–19 and 21; Table 5, #24–26; Table 6, 33–35; and Table 7, #36–39.

EXAMPLE XXII

Example XVI was repeated melt blending under inert gas 100 parts by weight of Kuraray (S-E-EP-S) 4077 multiblock copolymer and 40 parts by weight of Duraprime 70 white oil. A first part of the molten gel was allowed to cool to room temperature, the remainder gel was heated under inert gas for an additional three hours at 300–325° F. and a second part of the gel was exuded (from a 7.15 mm diameter orifice) into cold running water, and the third and final remaining gel was allowed to cool to room temperature. The bulk gel rigidities of the first, second and third parts were found to be within the range of 2 to 1,800 gram Bloom. The second and third final parts of the gel appeared to be altered and different from the first gel part. The first part exhibited rapid return when extended, but the second and third final parts exhibited delay elastomeric recovery when released after extension and deformation. All of the samples exhibited 100% recovery after repeated extensions and deformations.

TABLE 3A

Flossing Cycles to Break

| Sample No. | Floss Type | cross-section size | [2]Floss amalgam molars to break | [3]Floss fronts to |
|---|---|---|---|---|
| 1 | [4]Unwaxed spongy nylon | 0.30 | 18 | 200+ |
| 2 | [5]Regular waxed nylon | 0.11 | 11 | 200+ |
| 3 | [6]Extra fine unwaxed nylon | 0.06 | 6 | 200+ |

TABLE 3B

Flossing Cycles to Break

| Sample No. | Floss Type | [1]Relaxed/extended dia. (mm) | [2]Floss amalgam molars to break | [3]Floss fronts to break |
|---|---|---|---|---|
| 4 | [7]Gel | 2.42/0.16 | 37 | 76 |
| 5 | [7]Gel | 2.63/0.17 | 29 | 83 |
| 6 | [7]Gel | 2.75/0.17 | 36 | 183 |
| 7 | [7]Gel | 2.83/0.20 | 20 | 74 |
| 8 | [8]Gel | 3.22/0.22 | 8 | 30 |
| 9 | [8]Gel | 2.48/0.31 | 4 | 20 |
| 10 | [8]Gel | 3.16/0.33 | 6 | 44 |
| 11 | [8]Gel | 2.86/0.24 | 5 | 29 |

TABLE 4

Tensile Strength of Gel Strands

| Sample No. | Number of Strands | Radius (mm) | Area (cm$^2$) | Failure (Kg) | Tensile (Kg/cm$^2$) |
|---|---|---|---|---|---|
| 12 | 3 | 1.325 | 0.165 | 9.00 | 54.54 |
| 13 | 4 | 1.250 | 0.196 | 9.50 | 48.39 |
| 14 | 4 | 1.421 | 0.253 | 9.50 | 37.44 |
| 15 | 5 | 1.359 | 0.290 | 12.5 | 43.08 |
| 16 | 2 | 2.14 | 0.287 | 14.0 | 48.78 |
| 17 | 2 | 1.55 | 0.151 | 11.5 | 75.95 |
| 18 | 2 | 1.17 | 0.086 | 8.50 | 98.84 |
| 19 | 2 | 1.322 | 0.109 | 9.0 | 81.96 |
| 20 | 6 | 1.375 | 0.356 | 14 | 39.32 |
| 21 | 2 | 1.445 | 0.131 | 10 | 76.33 |
| 76 | 1 | 1.22 | 0.0467 | 2.00 | 42.82 |
| 77† | 1 | 1.38 | 0.0598 | 4.00 | 66.88 |

†Plasticizing oil extracted

TABLE 5

Tensile Strength of Bulk Gels Samples

| Sample No.. | Cross-section (cm$^2$) | Failure (Kg) | Tensile (Kg/cm$^2$) |
|---|---|---|---|
| 22 | 1.96 | 24.0 | 12.24 |
| 23 | 1.56 | 25.0 | 16.02 |
| 24 | 0.58 | 15.0 | 25.83 |
| 25 | 0.602 | 16.0 | 26.54 |
| 26 | 1.163 | 24.0 | 20.64 |
| 27 | 0.913 | 21.0 | 23.00 |
| 28 | 0.595 | 18.5 | 36.56 |
| 29 | 0.702 | 19.0 | 27.06 |

TABLE 6

180° U Bend Tear Propagation of Bulk Gels Samples

| Sample No. | Tear width (cm) | Failure (Kg) | Tear Force (Kg/cm) |
|---|---|---|---|
| 30 | 1.31 | 2.75 | 2.09 |
| 31 | 1.28 | 3.0 | 2.30 |
| 32 | 1.14 | 2.75 | 2.56 |
| 33 | 1.53 | 2.75 | 1.79 |
| 34 | 1.27 | 2.25 | 1.76 |
| 35 | 1.26 | 2.25 | 1.77 |

TABLE 7

Notched Gel Strand Tension Tear Propagation

| Sample No. | Strand Dia. (mm) | Failure (Kg) | Tear Force (Kg/cm) |
|---|---|---|---|
| 36 | 2.86 | 0.75 | 2.62 |
| 37 | 2.49 | 0.75 | 3.01 |
| 38 | 3.09 | 0.60 | 1.94 |
| 39 | 2.62 | 0.70 | 2.67 |
| 40 | 2.54 | 0.60 | 2.36 |
| 41 | 1.94 | 1.10 | 5.67 |
| 42 | 1.58 | 0.75 | 4.74 |
| 43 | 2.34 | 1.2 | 5.12 |

The tensile strengths of gels made from higher viscosity copolymer are lower than the tensile strengths of gels made from lower solution viscosity copolymers. This was later found to be due to orientation effects and not considered significant.

The tear resistance of gels made from higher viscosity copolymers are higher than the tear resistance of gels made from lower solution viscosity copolymers.

Gel strands made from higher viscosity copolymers perform better than gel strands made of lower viscosity copolymers when used in flossing amalgam molars and more than three times better when used in flossing front teeth.

As compared to spongy nylon, regular waxed nylon, and extra fine unwaxed nylon when flossing amalgam molars, the performance of gels are on the average substantially better.

Examples below illustrate other modes of practice contemplated.

EXAMPLE XXIII

At least 120 PCs of the gel strands of EXAMPLE XVI containing 600 parts oil is individually weighted and placed in a heated vacuum oven, a partial vacuum is applied and the temperature is regulated between about 80° F. to about 150° F. to extract plasticizer from the gel strands. At various oven and vacuum times, three gel strands are removed from the vacuum oven, allowed to cool to room temperature, weighted to determine the amount of weight loss and tested for tensile and tear strength. As the amount of oil contained in the original gel is reduced from 600 parts by weight to less than 200 parts by weight, the "reduced plasticizer volume" gels are weighted and tested The tea and tensile strengths of the reduced plasticizer volume gels are found to be improved over the properties of the original 600 parts by weight referenced gel strands.

The gels are especially advantageously useful when subjected to conditions of stretching, shearing, and tearing during flossing. The gels useful for flossing are characterized by low rigidities and high solution viscosity of the gels made from multiblock copolymers having two or more midblock polymer chains.

Tables 8–11 are illustrative in meeting one or more of the criteria detailed above.

8. Illustrative Modes of Practice Contemplated for multiblock copolymer Gels

| 100 Parts by wt | 5 Wt % Copolymer Viscosity (cps) | Styrene % | Parts by Wt of Oil | Number of floss cycles to break | Sample No. |
|---|---|---|---|---|---|
| S-E-EP-S | 90 | 30 | 300 | 30+ | 44 |
| S-E-EP-E-S | 60 | 30 | 300 | 30+ | 45 |
| (S-E-EP)n | 240 | 35 | 300 | 30+ | 46 |
| (S-E-EP-E)n | 240 | 35 | 300 | 30+ | 47 |
| S-B-EP-S | 90 | 30 | 300 | 30+ | 48 |
| S-E-EB-S | 90 | 35 | 300 | 30+ | 49 |
| S-EB-EP-S | 90 | 30 | 300 | 30+ | 50 |
| S-E-EP-EP-S | 90 | 30 | 300 | 30+ | 51 |

TABLE 9

Illustrative Modes of Practice Contemplated for multiblock copolymer Gels

| 100 Parts by wt | 5 Wt % Copolymer Viscosity (cps) | Styrene % | Parts by Wt of Oil | Number Floss cycles to Break | Sample No. |
|---|---|---|---|---|---|
| S-E-EP-EB-S | 120 | 33 | 250 | 30+ | 52 |
| S-E-EP-EP-S | 120 | 33 | 250 | 30+ | 53 |
| (S-B-EP)n | 380 | 35 | 250 | 30+ | 54 |
| (S-E-EB)n | 380 | 35 | 250 | 30+ | 55 |
| S-E-EP-E-EP-S | 120 | 30 | 250 | 30+ | 56 |
| S-E-EP-P-S | 120 | 35 | 250 | 30+ | 57 |
| S-E-B-EP-S | 120 | 30 | 250 | 30+ | 58 |
| S-E-EP-EP-E-S | 120 | 30 | 250 | 30+ | 59 |

TABLE 10

Illustrative Modes of Practice Contemplated for multiblock copolymer (0.5–2.0 cm diameters) Gel Strands

| 100 Parts by wt | 5 Wt % Copolymer Viscosity (cps) | Styrene % | Parts by Wt of Oil | # Floss cycles to Break | Sample No. |
|---|---|---|---|---|---|
| S-E-EP-S | 40 | 30 | 350 | 30+ | 60 |
| S-E-EP-S | 60 | 30 | 350 | 30+ | 61 |
| (S-E-EP-EB)n | 340 | 30 | 350 | 30+ | 62 |
| (S-E-EP-EP-E)n | 340 | 30 | 350 | 30+ | 63 |
| S-E-EP-E-EP-E-S | 90 | 30 | 350 | 30+ | 64 |
| S-EB-EP-EP-S | 90 | 35 | 350 | 30+ | 65 |
| S-B-EB-B-S | 90 | 30 | 350 | 30+ | 66 |
| S-E-EP-EP-E-S | 90 | 30 | 350 | 30+ | 67 |

TABLE 11

Illustrative Modes of Practice Contemplated for multiblock copolymer (0.5–2.0 cm diameters) Gel Strands

| 100 Parts by wt | 5 Wt % Copolymer Viscosity (cps) | Styrene % | Parts by Wt of Oil | # Floss cycles to Break | Sample No. |
|---|---|---|---|---|---|
| S-E-EB-S | 120 | 30 | 250 | 40+ | 68 |
| S-E-EP-S | 120 | 30 | 250 | 40+ | 69 |
| (S-E-EB)n | 280 | 35 | 250 | 40+ | 70 |

TABLE 11-continued

Illustrative Modes of Practice Contemplated for multiblock copolymer (0.5–2.0 cm diameters) Gel Strands

| 100 Parts by wt | 5 Wt % Copolymer Viscosity (cps) | Styrene % | Parts by Wt of Oil | # Floss cycles to Break | Sample No. |
|---|---|---|---|---|---|
| (S-E-EP)n | 280 | 35 | 250 | 40+ | 71 |
| S-E-EP-E-S | 120 | 30 | 250 | 40+ | 72 |
| S-EP-E-EP-S | 120 | 30 | 250 | 40+ | 73 |
| S-EB-E-EB-S | 120 | 30 | 250 | 40+ | 74 |
| S-EB-EB-S | 120 | 30 | 250 | 40+ | 75 |

While preferred components and formulation ranges have been disclosed herein persons of skill in the art can extend these ranges using appropriate material according to the principles discussed herein. Furthermore, Crystalline midblock segment block polymers can be use in blending with other engineering plastics and elastomeric polymers to make alloyed compositions having improved impact and tear resistance properties. All such variations and deviations which rely on the teachings through which the present invention has advanced the art are considered to be within the spirit and scope of the present invention.

What I claim is:

1. An improved gelatinous composition comprising: a crystal gel formed from (i) 100 parts by weight of one or more linear triblock copolymers, multi-arm block copolymers, branched block copolymers, radial block copolymers, multiblock copolymers, poly(ethylene-styrene) random copolymers produced by metallocene catalysts, using single site, constrained geometry addition polymerization catalysts resulting in poly(ethylene-styrene) substantially random copolymers, or thermoplastic crystalline polyurethane copolymers with hydrocarbon midblocks or a mixture of two or more said copolymers having one or more crystalline poly(ethylene) components (ii) from about 250 to about 1,600 parts of a plasticizer sufficient to achieve a gel rigidity of from less than about 2 gram Bloom to about 1,800 gram Bloom; wherein said crystalline poly(ethylene) components of said (i) copolymer having a selected amount of crystallinity sufficient to achieve improvements in one or more crystal gel properties including improved tear resistance and improved resistance to fatigue; wherein said improvements in properties of said crystal gel being greater than an amorphous gel made from poly(styrene-ethylene-butylene-styrene) or poly(styrene-ethylene-propylene-styrene) having substantially non-crystalline components at corresponding said gel rigidity; in combination with or without a selected amount of (iii) one or more of a selected polymer copolymer.

2. A crystal gel according to claim 1, wherein said gel having a selected crystallinity as exhibited in differential scanning calorimeter (DSC) a melting endotherm values of about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C. or higher.

3. A crystal gel according to claim 1, wherein said copolymer having a selected crystallinity as exhibited in differential scanning calorimetry (DSC) a melting endotherm values of about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60°

C., 61° C., 62° C., 63° C., 64° C., 65° C., 66° C., 67° C., 68° C., 69° C., 70° C., 71° C., 72° C., 73° C., 74° C., 74° C., 75° C., 76° C., 77° C., 78° C., 79° C., 80° C. or higher.

4. A crystal gel according to claim 1, wherein said crystal gel is formed from said (i) copolymer in combination with or without a selected amount of (iii) one or more polymer or copolymer of poly(styrene-butadiene-styrene), poly (styrene-butadiene), poly(styrene-isoprene-styrene), poly (styrene-isoprene), poly(styrene-ethylene-propylene), poly (styrene-ethylene-propylene-styrene), poly(styrene-ethylene-butylene-styrene), poly(styrene-ethylene-butylene), poly(styrene-ethylene-propylene)n, poly(styrene-ethylene-butylene)n, maleated poly(styrene-ethylene-propylene-styrene), maleated poly(styrene-ethylene-butylene-styrene), maleated poly(styrene-ethylene-butylene), maleated poly(styrene-ethylene-propylene)n, maleated poly(styrene-ethylene-butylene)n, polystyrene, polybutylene, poly(ethylene-propylene), poly(ethylene-butylene), polypropylene, polyethylene, polyethylene copolymers, polyethyleneoxide, poly(dimethylphenylene oxide), copolymers of trifluoromethyl-4,5difuoro-1,3-dioxole and tetrafluoroethylene, tetrafluoroethylene, polycarbonate, ethylene vinyl alcohol copolymer, polyamide, polyethyleneoxide, poly(dimethylphenylene oxide), polystyrene, polybutylene, polyethylene, polypropylene, high ethylene content EPDM, amorphous copolymers based on 2,2-bistrifluoromethyl-4,5-difuoro-1, 3-dioxole/tetrafluoroethylene or polydimethylsiloxane; wherein said (i)copolymer and said (iii) copolymer is a linear, branched, radial, or a multiarm copolymer.

5. A composite comprising a crystal gel of claim 1, where said gel is denoted by G being physically interlocked with a selected material M forming the combination $G_nM_n$, $G_nM_nG_n$, $M_nG_nM_n$, $M_nG_nG_nM_n$, $G_nM_nM_nG_n$, $G_nM_nG_nM_nG_n$, $M_nM_nM_nG_n$, $M_nM_nM_nG_nM_nM_nM_n$, $G_nG_n$, $G_nG_nG_n$, $M_nG_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_nG_nM_n$, $G_nM_nG_nG_n$, $G_nM_nG_nM_nM_n$, $M_nG_nM_nG_nG_n$, or a permutation of one or more of said $G_n$ with $M_n$; wherein when n is a subscript of M, n is the same or different selected from the group consisting of paper, foam, plastic, natural fibers, fabric, metal, metal foil, concrete, wood, glass, glass fibers, ceramics, synthetic resin, synthetic fibers or refractory materials; and wherein when n is a subscript of G, n denotes the same or a different gel rigidity.

6. A prosthetic device comprising a lower extremity socket insert for below the knee or above the knee with or without a cuff suspension formed from a crystal gel of claim 1.

7. A prosthetic device comprising a lower extremity socket insert for below the knee or above the knee with or without a cuff suspension formed from a crystal gel composite claim 5, wherein M is a fabric.

8. A crystal gel of claim 1, wherein said crystal gel is formed from said copolymer and one or more polyphenolic low coefficient of friction agents in combination with one or more of an internal nucleating agent or one or more of an external nucleating agent sufficient to achieve a coefficient of friction of less than 1.0 to about less than 0.40.

9. A dental floss comprising a crystal gel of claim 1, wherein said floss is formed into a strand, thread, tape, or yarn suitable for use as a dental floss.

10. A low tack gelatinous composition comprising: a crystal gel formed from (i) 100 parts by weight of one or more copolymers having a selected amount of one or more elastomeric segments and a selected amount of one or more glassy segments, said elastomeric segments having a selected amount of one or more crystalline poly(ethylene) components and said glassy segments being a poly(styrene), poly(alpha-methylstyrene), poly(o-methylstyrene), poly(m-methylstyrene), or poly(p-methylstyrene);

(ii) from about 250 to about 1,600 parts of a plasticizer sufficient to achieve a gel rigidity of from less than about 2 gram Bloom to about 1,800 gram Bloom;

(iii) said low tack being achieved by a combination of said selected amount of crystalline poly(ethylene) components of said selected amount of said glassy segments forming said crystal gel, wherein said elastomeric segments and said glassy segments being a ratio of about 37:63 and said tack of said crystal gel being less than amorphous gels of poly(styrene-ethylene-butylene-styrene) or poly(styrene-ethylene-propylene-styrene) of substantially same rigidities.

11. An improved gelatinous composition comprising: a crystal gel formed from (i) 100 parts by weight of one or more of a substantially random poly(ethylene-styrene) copolymers produced by metallocene catalysts or in combination as a mixture with or without one or more of (a) a linear triblock copolymers, (b) multi-arm block copolymers, (c) branched block copolymers, or (d) radial block copolymers, said substantially random poly(ethylene-styrene), linear triblock, multi-arm block, branched block, and radial block copolymers having one or more crystalline poly(ethylene) components (ii) from about 250 to about 1,600 parts of a plasticizer sufficient to achieve a gel rigidity of from less than about 2 gram Bloom to about 1,800 gram Bloom; wherein said crystalline poly(ethylene) components of said substantially random copolymer and said (a), (b), (c), (d) copolymers having a selected amount of crystallinity sufficient to achieve improvements in one or more crystal gel properties including improved tear resistance and improved resistance to fatigue; wherein said improvements in properties of said crystal gel being greater than an amorphous gel made from poly(styrene-ethylene-butylenestyrene) or poly (styrene-ethylene-propylene-styrene) having substantially non-crystalline components at corresponding said gel rigidity; in combination with or without a selected amount of (iii) one or more of a selected polymer or copolymer.

12. A composite comprising a crystal gel of claim 11, where said gel is denoted by G being physically interlocked with a selected material M forming the combination $G_nM_n$, $G_nM_nG_n$, $M_nG_nM_n$, $M_nG_nG_nM_n$, $G_nM_nM_nG_n$, $G_nM_nG_nM_nG_n$, $M_nM_nM_nG_n$, $M_nM_nM_nG_nM_nM_nM_n$, $G_nG_n$, $G_nG_nG_n$, $M_nG_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_nG_nM_n$, $G_nM_nG_nG_n$, $G_nM_nG_nM_nM_n$, $M_nG_nM_nG_nG_n$, or a permutation of one or more of said $G_n$ with $M_n$; wherein when n is a subscript of M, n is the same or different selected from the group consisting of paper, foam, plastic, natural fibers, fabric, metal, metal foil, concrete, wood, glass, glass fibers, ceramics, synthetic resin, synthetic fibers or refractory materials; and wherein when n is a subscript of G, n denotes the same or a different gel rigidity.

13. A crystal gel according to claim 11, wherein said copolymer having a selected amount of about 20%, 22%, 25%, 30%, 40%, 50%, 60%, 65%, or about 70% of $(-CH2-)^{16}$ units of the total mole % forming the midblocks of the substantially random copolymer so as to exhibit in differential scanning calorimetry (DSC) a crystallinity melting endotherm values of about 20° C., 21° C., 22° C., 23° C., 24° C., 25° C., 26° C., 27° C., 28° C., 29° C., 30° C., 31°

C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C. or higher.

14. A crystal gel according to claim 11, wherein said copolymer having a selected amount of about 20%, 22%, 25%, 30%, 40%, 50%, 60%, 65%, or about 70% of $(—CH2-)^{16}$ units of the total mole % forming the midblocks of the substantially copolymer so as to exhibit in differential scanning calorimetry (DSC) a crystallinity melting endotherm values of about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 74° C., 75° C., 76° C., 77° C., 78° C., 79° C., 80° C., or higher.

* * * * *